(12) United States Patent
Akdis

(10) Patent No.: US 9,616,157 B2
(45) Date of Patent: Apr. 11, 2017

(54) BLOOD PUMP

(76) Inventor: Mustafa Akdis, Merenberg (DE)

(\*) Notice: Subject to any disclaimer, the term of this patent is extended or adjusted under 35 U.S.C. 154(b) by 0 days.

(21) Appl. No.: 12/376,549

(22) PCT Filed: Aug. 1, 2007

(86) PCT No.: PCT/DE2007/001374
§ 371 (c)(1),
(2), (4) Date: Jun. 8, 2009

(87) PCT Pub. No.: WO2008/017289
PCT Pub. Date: Feb. 14, 2008

(65) Prior Publication Data
US 2011/0238172 A1 Sep. 29, 2011

(30) Foreign Application Priority Data
Aug. 6, 2006 (DE) .................. 10 2006 036 948

(51) Int. Cl.
| A61M 1/10 | (2006.01) |
| F04D 13/06 | (2006.01) |
| F16C 32/04 | (2006.01) |
| F16C 32/06 | (2006.01) |

(52) U.S. Cl.
CPC .......... *A61M 1/101* (2013.01); *A61M 1/1015* (2014.02); *A61M 1/1017* (2014.02); *A61M 1/1036* (2014.02); *F04D 13/0666* (2013.01); *F16C 32/048* (2013.01); *F16C 32/0629* (2013.01); *F16C 32/0685* (2013.01)

(58) Field of Classification Search
CPC .. A61M 1/101; A61M 1/1015; A61M 1/1036; A61M 1/1017; A61M 1/1031; A61M 1/10; F04D 13/0666; F16C 32/0629; F16C 32/048; F16C 32/0685
USPC ............... 415/229, 900, 104, 105, 106, 107; 417/420
See application file for complete search history.

(56) References Cited

U.S. PATENT DOCUMENTS

| 5,112,200 A | 5/1992 | Isaacson et al. |
| 5,840,070 A | 11/1998 | Wampler |
| 6,071,093 A * | 6/2000 | Hart .......................... 417/424.2 |
| 6,135,710 A | 10/2000 | Araki et al. |

(Continued)

FOREIGN PATENT DOCUMENTS

| AU | 760610 | 11/2000 |
| AU | 760 610 | 5/2003 |

(Continued)

OTHER PUBLICATIONS

Akdis M, Martin M, Reul H; "Lomakin Bearing for an Implantable Rotary Blood Pump", Jul. 2004, International Journal of Artificial Organs, vol. 27 (7), p. 599.*

(Continued)

*Primary Examiner* — Dwayne J White
*Assistant Examiner* — Adam W Brown
(74) *Attorney, Agent, or Firm* — Clark & Brody

(57) ABSTRACT

There is provided a blood pump. An exemplary blood pump comprises an impeller with a rotational axis in a pump housing. The exemplary blood pump also comprises a first element that comprises a Lomakin bearing, and a second element physically separated from the first element, the second element comprising a radial magnetic bearing.

19 Claims, 21 Drawing Sheets

(56) References Cited

U.S. PATENT DOCUMENTS

| | | | |
|---|---|---|---|
| 6,227,820 B1 | 5/2001 | Jarvik | |
| 6,234,772 B1 | 5/2001 | Wampler et al. | |
| 6,239,901 B1 | 5/2001 | Kaneko | |
| 6,250,880 B1 * | 6/2001 | Woodard et al. | 415/182.1 |
| 6,293,901 B1 | 9/2001 | Prem | |
| 6,394,769 B1 * | 5/2002 | Bearnson et al. | 417/423.7 |
| 6,620,188 B1 * | 9/2003 | Ginsburg et al. | 607/106 |
| 6,623,475 B1 | 9/2003 | Siess | |
| 6,722,863 B2 * | 4/2004 | Maeda et al. | 417/420 |
| 7,682,301 B2 | 3/2010 | Wampler et al. | |
| 2004/0091354 A1 | 5/2004 | Araki et al. | |
| 2006/0024182 A1 * | 2/2006 | Akdis et al. | 417/423.12 |

FOREIGN PATENT DOCUMENTS

| | | |
|---|---|---|
| DE | 69828926 T2 | 6/2006 |
| EP | 0901797 A2 | 3/1999 |
| WO | 98/11650 | 3/1998 |
| WO | WO9811650 | 3/1998 |
| WO | 2004/089677 | 10/2004 |
| WO | WO2004098677 | 11/2004 |
| WO | 2004/106746 | 12/2004 |
| WO | WO2004106746 | 12/2004 |
| WO | 2005/002800 | 1/2005 |
| WO | WO2005028000 | 3/2005 |
| WO | 2005/090791 | 9/2005 |
| WO | WO2005090792 | 9/2005 |

OTHER PUBLICATIONS

Marscher, W; "The relationship of vibration to problems in centrifugal pumps: vibration analysis, when properly carried out, can help keep your pumps operating troublefree."; May 2004; Chemical Engineering; vol. 111, p. 38(7).*

PCT International Preliminary Report on Patentability, International Application No. PCT/DE2007/001374, International Filing Date Aug. 1, 2007, Translation.

* cited by examiner

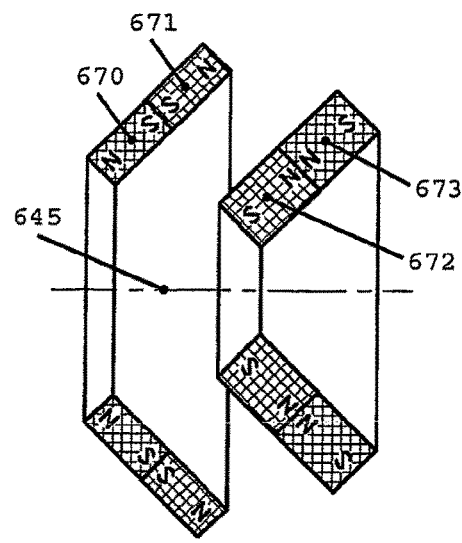
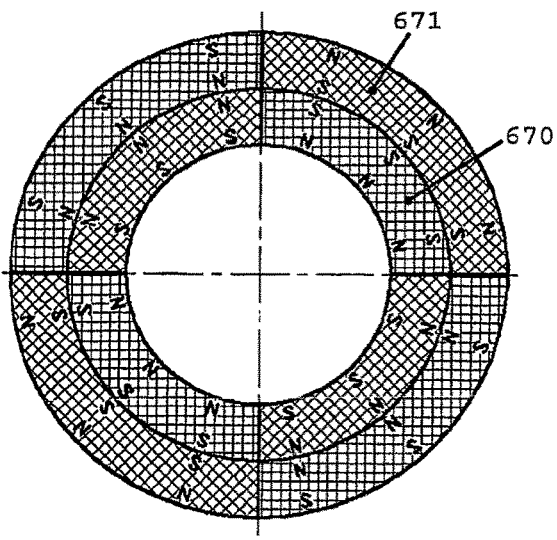
Fig. 28  Fig. 29
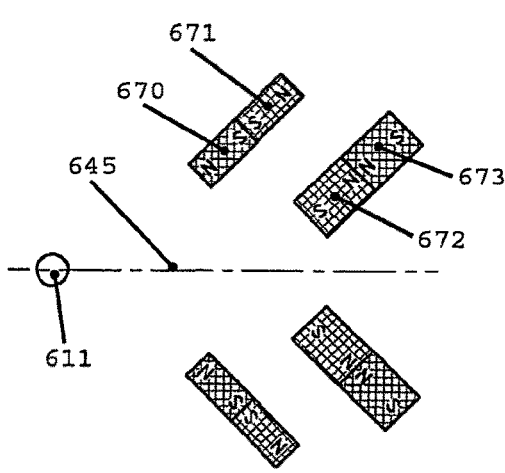
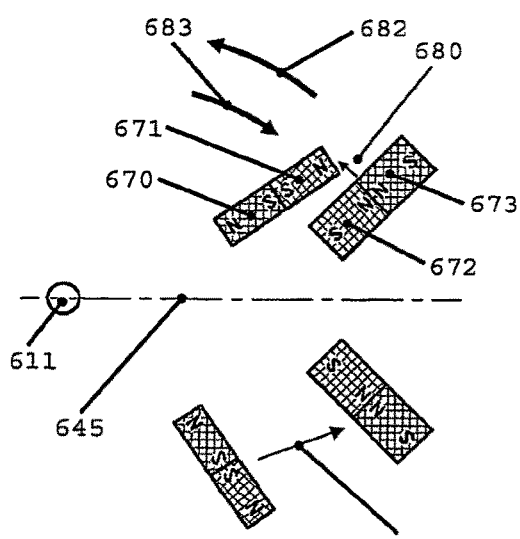
Fig. 30  Fig. 31 kreisförmig · elliptisch

BLOOD PUMP

CROSS REFERENCE TO RELATED APPLICATIONS

Pursuant to 35 U.S.C. §371, this application is the United States National Stage Application of International Patent Application No. PCT/DE2007/001374, filed on Aug. 1, 2007, the contents of which are incorporated by reference as if set forth in their entirety herein, which claims priority to German (DE) Patent Application No. 102006036948.3, filed Aug. 6, 2006, the contents of which are incorporated by reference as if set forth in their entirety herein.

BACKGROUND

Over the course of the past decades, mechanical heart support systems have become more and more prevalent as a therapeutic method for treating chronic cardiac insufficiency. Their main task consists of maintaining blood circulation, thus ensuring an adequate supply of oxygen to organs and tissues in cases of heart failure. More recent developments in the realm of mechanical circulatory support systems have led to the creation of numerous pump mechanisms which, depending on the clinical indication, range from unilateral ventricular assist devices (VAD) to total heart replacement or artificial heart (TAH) systems. It is common knowledge in the realm of heart surgery nowadays that the clinical demand for ventricular assist devices is considerably higher than the demand for total artificial heart systems, and left-ventricular assist devices (LVAD) are of special significance due to the higher hemodynamic load on the left half of the heart. A major therapeutic objective of an assist device is to provide a "bridge-to-transplant", wherein the VAD system takes over or assists the pumping capacity of the insufficient heart until a suitable donor organ becomes available and a heart transplantation can be performed. According to pertinent statistics, approximately 70% of the patients with mechanical assist systems reach the stage of heart transplantation, which is then performed with a mortality rate of less than 10% (Hammel et al., Mechanische myokardiale Unterstützungsysteme [Mechanical myocardial assist systems] 1997, published in the journal Anaesthesist, No. 46, pages 408-418, 1997). A more in-depth treatment of the clinical and technical aspects and special features of VAD and TAH systems has been provided by Akdis et al. (Handbuch der Kardiotechnik [Manual of cardiotechnology], 4$^{th}$ Edition, pages 461-482, published by Urban & Fischer Verlag, 2002), and by Hetzer et al. [Kardiale Assist-Systeme: Gegenwärtiger Stand [Cardiac assist systems: current status] in the journal Herz, No. 5, pages 407-417, published by Urban & Fischer Verlag, 2002).

German publication DE 698 28 962 T2 discloses a blood pump with an impeller. Here, the blood pump has an inlet and an outlet. In this blood pump, the impeller is radially supported by two magnetic bearings. Moreover, the impeller is stabilized in the radial direction by a hydrodynamic bearing in the form of raised surfaces and contact surfaces. When the impeller turns, these hydrodynamic bearings cause the impeller to be separated from the housing by means of a liquid film. The functionality of this hydrodynamic bearing is based on constricted bearing gap geometries that are formed by several bearing elements whose shape is rectangular or tapered.

SUMMARY OF THE INVENTION

Exemplary embodiments of the present invention relate to a blood pump. In particular, an exemplary blood pump relates to conveying blood in extracorporeal circulation systems, preferably over a short to medium period of time (from 6 hours to 6 months) as well as in intracorporeal circulation systems over a long period of time (from 6 months to 10 years).

Therefore, an exemplary embodiment of the present invention may relate to a blood pump that allows it to be used in a manner that is gentle on patients in various clinical applications and for various periods of time.

This objective may be achieved in an exemplary embodiment of the present invention by a device for conveying blood, especially a rotary pump, whose structure and mode of operation in terms of the pump design, drive concept, flow pattern and especially rotor bearings are gentle on the blood when used for patients over the during the period of time in question.

An exemplary embodiment of the invention comprises a blood pump having an impeller with a rotational axis in a pump housing, whereby the blood pump has an inlet and an outlet.

According to an exemplary embodiment of the invention, the blood pump comprises at least two elements that are physically separated from each other, whereby at least one of the elements is constructed in such a way that it has a fluid-mechanically stabilizing effect in a radial directional component and that at least another element constitutes a radial magnetic bearing.

It may be advantageous for the fluid-mechanically stabilizing element to be formed by the pump housing and by a pump impeller and/or by a component of the pump impeller.

The term "fluid-mechanically stabilizing" particularly relates to a bearing, preferably a fluid-mechanical radial bearing.

It may be advantageous for the radial magnetic bearing to be an electromagnetic radial bearing.

It may be advantageous for the radial magnetic bearing to be a permanent magnetic radial bearing.

It may be advantageous for the radial magnetic bearing to be formed by a magnetic coupling.

It may be advantageous for the radial magnetic bearing to comprise at least two annular magnets.

It may be advantageous for at least one of the annular magnets to be integrated into the pump impeller and/or into one of the components of the pump impeller.

It may be advantageous for the radial magnetic bearing to function by means of repulsive magnetic forces.

It may be advantageous for the radial magnetic bearing to function by means of attractive magnetic forces.

It may be advantageous for the radial magnetic bearing to be configured as a separate permanent magnetic radial bearing.

It may be advantageous for the radial magnetic bearing to be configured as a separate electromagnetic radial bearing.

It may be advantageous for the radial magnetic bearing to have a rotor magnet in the impeller and a stator magnet in the pump housing.

It may be advantageous for the radial magnetic bearing to be integrated into a magnetic coupling.

It may be advantageous for the magnetic coupling to be an axial magnetic coupling.

It may be advantageous for the magnetic coupling to be a diagonal magnetic coupling.

It may be advantageous for the radial magnetic bearing to exert regulated electromagnetic forces.

It may be advantageous for the fluid-mechanically stabilizing element to be operational between the impeller and the pump housing.

It may be advantageous for the fluid-mechanically stabilizing element to be operational between the shroud and the pump housing.

It may be advantageous for the fluid-mechanically stabilizing element to be operational between the impeller blades and the pump housing.

BRIEF DESCRIPTION OF THE DRAWINGS

The figures show details of the blood pump according to an exemplary embodiment of the present invention or of parts thereof in schematic form. In particular, the figures show the following:

FIG. 28 is a diagram showing the diagonal coupling of FIG. 24 with a separation of the coupling magnets in the radial direction;

FIG. 29 is a cross-section view through the diagonal coupling of FIG. 28;

FIG. 30 is a diagram of the diagonal coupling of FIG. 28 in a state of balance;

FIG. 31 is a diagram of the diagonal coupling of FIG. 28 in a deflected position, and the bearing forces that are thus active in the diagonal of coupling;

DETAILED DESCRIPTION OF SPECIFIC EMBODIMENTS

Figure 1:
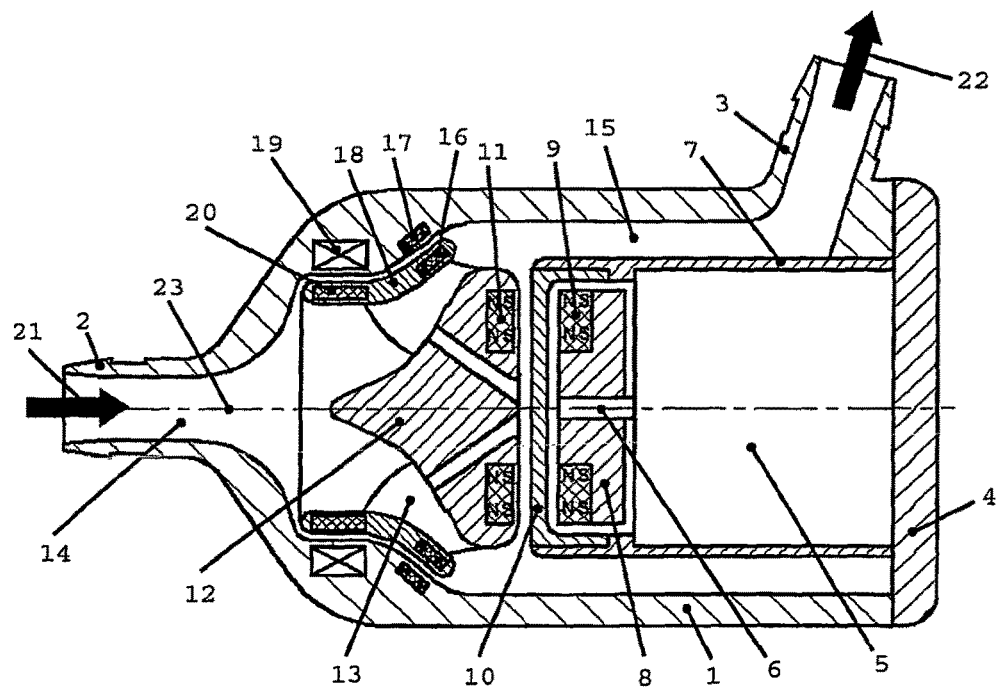
FIG. 1 is a cut-away view of a blood pump with an electromagnetic rotor bearing in which an integrated electric motor with a permanent magnetic axial coupling is employed as the drive according to an exemplary embodiment of the present invention.

Examples of preferred mechanisms of action are:

Radial fluid-mechanical stabilization based on hydrostatic forces, for example, a Lomakin effect between the impeller and the pump housing, or between the shroud and the pump housing, or between the impeller blades and the pump housing, and/or a choke gap effect, likewise between the impeller and the pump housing, and/or between the shroud and the pump housing, and/or between the impeller blades and the pump housing.

Additional examples of preferred mechanisms of action for the radial fluid-mechanical stabilization are based on hydrodynamic forces (Reynolds effect) between the impeller and the pump housing, and/or between the shroud and the pump housing, and/or between the impeller blades and the pump housing, or else they are based on hydraulic forces between the impeller and the pump housing, and/or between the shroud and the pump housing, and/or between the impeller blades and the pump housing.

It may be advantageous for the blood pump to have an axial bearing of the impeller.

It may be advantageous for the axial bearing of the impeller to be based on permanent magnetic forces.

It may be advantageous for the axial bearing of the impeller to be based on electromagnetic forces.

It may be advantageous for the axial bearing of the impeller to be based on fluid-mechanical forces.

Examples of the axial bearing of the impeller are:
a) Magnetic axial bearing
  i) based on permanent magnetic forces
    1) separate permanent magnetic axial bearing (rotor magnet in the impeller, stator magnet in the pump housing)
      a) repulsive magnetic forces
        i) annular configuration of the rotor magnet and of the stator magnet
        ii) axially offset arrangement of the rotor magnet and of the stator magnet
      b) attractive magnetic forces
        i) annular configuration of the rotor magnet and of the stator magnet
        ii) axially offset arrangement of the rotor magnet and of the stator magnet
    2) axial bearing integrated into the permanent magnetic coupling
      a) based on a radial magnetic coupling
      b) based on a diagonal magnetic coupling
  ii) based on electromagnetic forces
    1) regulated magnetic forces
      a) active magnetic bearing (stator magnet in the housing, rotor magnet in the impeller)
        i) based on a radial active magnetic bearing
        ii) based on a diagonal active magnetic bearing
    2) unregulated electromagnetic forces
      a) electromagnetic coupling
        i) based on an axial magnetic coupling
        ii) based on a diagonal magnetic coupling
b) Fluid-mechanical axial bearing (between the impeller and the pump housing)
  1) hydrodynamic axial bearing
  2) hydrostatic axial bearing
  3) hydraulic axial bearing
c) Mechanical axial bearing (between the impeller and the pump housing)
  1) pivot bearing (thrust ball bearing)

Advantageously, the pump design may be characterized by a harmonious flat design, wherein the pump housing and/or the electric motor preferably have an elliptical cross section.

Examples of preferred drive concepts are:
A) a blood pump according to one of the preceding items, whereby the blood pump is configured as a separable pump head and is driven by an external (re-useable) drive unit;
B) the blood pump according to A), whereby the drive unit essentially comprises an electric motor and/or a magnetic coupling device;
C) the blood pump and/or the method according to A), whereby the drive unit is a turbine powered by high-pressure gas;
D) the blood pump and/or the method according to C), whereby high-pressure oxygen is employed as the high-pressure gas;
E) the blood pump and/or the method according to D), whereby oxygen is concurrently employed for blood oxygenation in a physically separated device.

Hydrostatic Radial Bearing and Hydrodynamic Axial Bearing:

It is practical for at least one of the electromagnetic elements to be a hydrostatic radial bearing.

Mechanical-Magnetic Rotor Bearing:

It is practical for the blood pump having a blade impeller with a rotational axis in a pump housing to be configured with a feed channel and with at least one mechanically contacting bearing device and with at least one permanent magnetic device in such a way that at least one mechanically contacting device is a thrust ball bearing and at least one permanent magnetic device is a permanent magnetic bearing that is unstable in the radial direction and stable in the axial direction.

It is practical for the permanent magnetic bearing to be essentially based on two annular magnets that are polarized oppositely with respect to each other.

Harmonious Flat Design:

It is practical for the height-to-width ratio of the pump housing to be less than 1.

Separable Pump Head with an Electromagnetic Drive;

It is practical for the blood pump to be separated from the drive unit and for the drive unit to be reusable.

Separable Pump Head with Pneumatic ($O_2$) Turbine Drive:

It is practical that, for the extracorporeal conveying of blood and oxygen, at least one high-pressure oxygen turbine is employed that is configured to be physically separable from the blood pump. Advantageously, the blood pump here is driven via a turbine.

An exemplary embodiment of the invention also relates to a device and to a method for the extracorporeal conveying of blood and oxygen, said device consisting of a blood pump, an oxygenation system, a gas turbine and a high-pressure oxygen reservoir, all of which are configured so as to be physically separate from each other.

It is practical for the turbine to be driven by the high-pressure oxygen reservoir, for the blood pump to be driven by the turbine, for the high-pressure oxygen reservoir to supply the oxygenator with oxygen and for the blood pump to convey blood through the oxygenator.

From an engineering standpoint, the VAD systems can be broken down into two main categories in terms of the effective pump mechanism:
1) displacement blood pumps,
2) rotary blood pumps.

Displacement blood pumps make up the first generation of cardiac assist blood pumps and are essentially comparable to a diaphragm pump. Due to the pulsatile volume change in a ventricle filled with blood, which is achieved by additional pneumatic, hydraulic and/or electromechanical energy—in a manner similar to a piston pump—a physiological pressure and flow are built up, so that blood is drawn out of the left ventricle and conveyed into the aorta. The fundamental advantage of these systems lies in their mode of operation which is pulsatile and thus replicates the natural heart, in contrast to which their larger size is problematic when it comes to implanting the pump, in addition to which their complex mode of operation makes them laborious to manufacture.

Consequently, rotary blood pumps are acquiring ever greater clinical significance in view of their simple structure and their minimal size. In contrast to displacement blood pumps, rotary blood pumps do not produce a pulsatile, but rather a continuous, blood flow through the pump, an aspect that, however, is seen as being physiologically acceptable by the medical community, even for long-term use over the course of several years (Schmid et al., Chirurgische Therapieoptionen bei schwerer Herzinsuffizienz [Surgical therapy options in cases of severe cardiac insufficiency], Deutsches Ärzteblatt, Vol. 101, Issue 7, pages 429-435).

Figure 40:
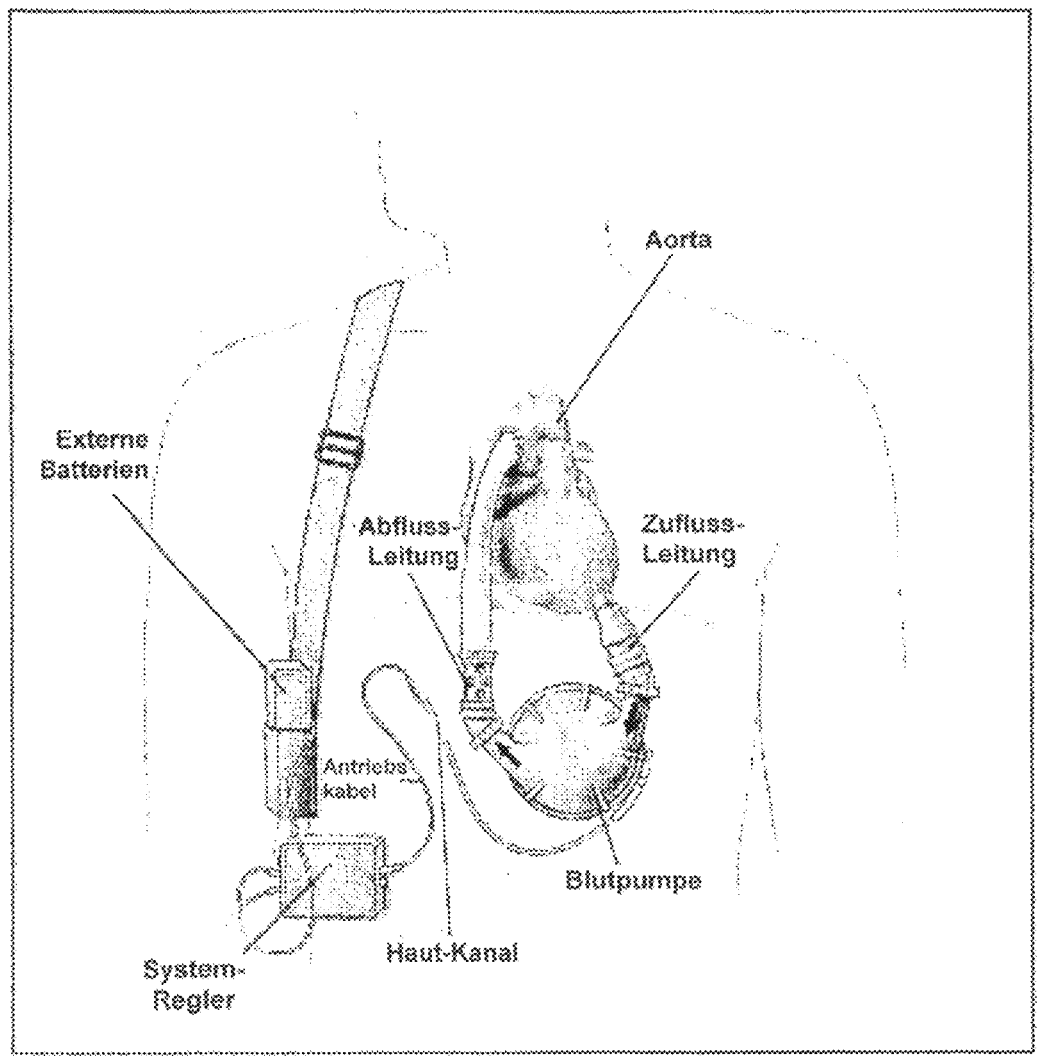
FIG. 40 is a diagram of an implantable blood pump as a VAD system.

The basic structure of a rotary blood pump comprises a rotatably mounted impeller (rotor) which, as a rule, is driven by an electric motor fitted with an appropriate coupling device and which converts the supplied rotational energy into hydraulic energy for purposes of building up pressure and flow, and it also comprises a pump housing that separates the pump components from the surroundings. In order to convey the fluid (blood) between the blood pump and the blood vessels, cannulas and grafts are employed that have to be fastened to the inlet and to the outlet of the pump. Moreover, the electronic control and regulation elements used to actuate the pump as well as the sensors to monitor the pump parameters can be housed in a separate controller unit. For purposes of mobile use of the pump, it is also possible to supply the energy via portable batteries. FIG. 40 schematically shows the use of a VAD in a blood pump as well as its accessories.

With an eye towards attaining simple handling and operation that is gentle on patients during clinical use, another very important aspect is the placement of the blood pump relative to the body of the patient. In principle, it can be said that, depending on the clinical use, a blood pump can be placed either outside of the body (extracorporeal) or else inside the body (intracorporeal). In the first case, a distinction is also made regarding those blood pump systems which, owing to their compact size, can be placed close to the patient (paracorporeal). When it comes to the intracorporeal placement of the blood pump, in contrast, a distinction is made between those systems that can be placed under the skin (subcutaneous), in the chest cavity (intrathoraxic), underneath the diaphragm (subdominal), inside a blood vessel (intravasal) or inside the ventricles themselves (intracardial, intraventricular).

It should be pointed out that, especially for brief application periods, for example, in a heart-lung machine (HLM) or for extracorporeal membrane oxygenation (ECMO) as well as for short-term to medium-term use as a VAD system for a period of time of up to 6 months, the rotary blood pump is usually placed extracorporeally, whereas for longer-term application periods, the blood pump is preferably accommodated inside the body in view of the infection risk entailed by open wounds. The precise placement of the pump in the body then depends primarily on the clinical indication and especially on the size and other technical properties of the blood pump. Nevertheless, the general goal in the development of an implantable rotary blood pump is to greatly diminish its size (which is defined by the main dimensions of the pump housing), thus minimizing contact of blood and tissues with surfaces that are foreign to the body.

Due to the rotating movement of the impeller, rotary blood pumps and especially their housings are primarily built in cylindrical form, whereby the diameter of the impeller essentially determines the main dimension of the rotary blood pump. However, an anatomically appropriate design for various clinical indications and implantation positions cannot be adequately achieved with a cylindrical outer contour of the pump, and so there is an increasing clinical need for a pump design that is adapted to the local anatomy of the human body.

An exemplary embodiment of the present invention may relate to a blood pump whose design permits its implantation into various regions of the human body.

Furthermore, the advantages of the use of a rotary pump are countered by certain risks and dangers stemming primarily from the special properties of blood as the physiological medium that is to be conveyed. First and foremost, mention should be made here of damage to the corpuscular blood constituents such as erythrocytes and thrombocytes, which can be traced back to the flow and temperature fields induced in the rotary blood pump as well as to the interaction of the blood with technical surfaces. Excessive shear stresses on erythrocytes can, for example, cause their cell walls to become damaged so that the hemolysis rate rises inordinately. On the other hand, there is also a need to avoid a sluggish flow and flow recirculation and also to keep the temperature of the pump components that come into contact with blood within the limits of physiological permissibility (blood temperature of approximately 37° C. [98.6° F.]), since a stagnating flow or an excessive warming of the blood entails the risk of thrombocyte activation and the resulting coagulation as well as a risk for the patients (infarction and embolism due to clots in peripheral blood vessels) and also the risk of pump failure. Therefore, the general guideline for the development of a rotary pump is that the flow through the pump should be designed specifically so as to avoid stagnating or recirculating flow areas (dead water spaces) as well as to considerably minimize shear stresses and temperature increases in the blood. Therefore, the localized danger zones in terms of hemolysis and thrombogenicity are the narrow side spaces between the impeller and the housing as well as, in particular, the rotor bearing of the impeller. The special features of the rotor bearing of a rotary blood pump, in contrast to conventional rotary pumps, in turn, have to do with the special properties of blood as the medium, so that it is often the case that the tried and true rotor bearing variants of classic machine construction are not readily suitable for use in a blood pump. Moreover, it is also necessary to take into account the work involved in the production of the rotor bearing of a blood pump.

A number of rotor bearing concepts exist for rotary blood pumps, and these can be broken down as follows:
1) ball bearing with shaft gaskets to seal the bearing vis-à-vis the blood,
2) sliding bearing in the blood,
3) contact-free magnetic bearing.

The advantage of the first variant is its simple structure, in contrast to which its short service life due to leaks at the gasket precludes its long-term use in a blood pump. The sliding bearings, in contrast, have a service life sufficient for at least medium-term applications but their design has to be optimized in such a way that the tribological conditions (bearing friction and heating) do not damage the blood. Finally, the magnetic bearings have the major advantage that they function contact-free and thus friction-free but, due to the demanding manufacturing work involved for the electromagnetic components of the magnetic bearing, they are not suitable for short-term applications.

Structure and mode of operation of the blood pump:
The structure and mode of operation of the blood pump according to an exemplary embodiment of the invention will be explained in greater detail by way of an example with reference to FIGS. 1 and 2.

In its entirety, the blood pump consists of the following five main components:
1) pump housing
2) drive unit
3) pump impeller
4) rotor bearing
5) flow pattern Within the scope of an exemplary embodiment of the present invention, especially the rotor bearing of the pump impeller in the pump housing plays a pivotal role so that the rotor bearing will be described in greater detail in the concluding part in conjunction with the description of the inventive novelty.

Pump Housing:
The pump housing (1) has an essentially hollow cylindrical form and, as the superordinated unit, its interior holds the other components of the blood pump. In the case of blood pumps having an external drive (that is to say, the drive is located outside of the interior of the pump housing), the blood pump comprises only the pump impeller, its rotor bearing\ as well as the flow pattern in the pump. Blood pumps having external drives as well as those pumps having integrated drives are taken into consideration within the scope of the present invention. The figures depicting exemplary embodiments of the invention as well as their descriptions will provide more in-depth information on this topic.

One end of the pump housing (1) is permanently connected to the pump inlet (2) and its other end is connected to the pump outlet (3). In the case of an integrated drive, a pump cover (4) closes off the interior of the pump housing (1) vis-à-vis the surroundings.

Drive Unit:
The drive unit serves essentially to maintain the rotational movement of the impeller. For blood pumps, the current state of the art uses exclusively drives that have an electric source of energy and are thus designed as electric motors. A special feature within the scope of an exemplary embodiment of the present invention is that a method and a device for conveying blood are being presented in which the drive is not supplied with electric energy, but rather, with pneumatic energy in an interaction with a turbine. This concept is particularly practical and effective for all applications for blood pumps where the turbine is driven by a source of high-pressure oxygen and oxygen is available in every operating room and in every hospital ward. Moreover, the combination of a blood pump with a blood oxygenation system (oxygenator) translates into a suitable synergism since oxygen can be employed for the oxygenation as well as to drive the pump. Particularly for short-term to medium-term applications (heart-lung machine, ECMO, etc.) involving extracorporeal placement of the blood pump, such a drive concept entails considerable advantages in comparison to electric motors in terms of reducing the effort involved.

Figure 22:
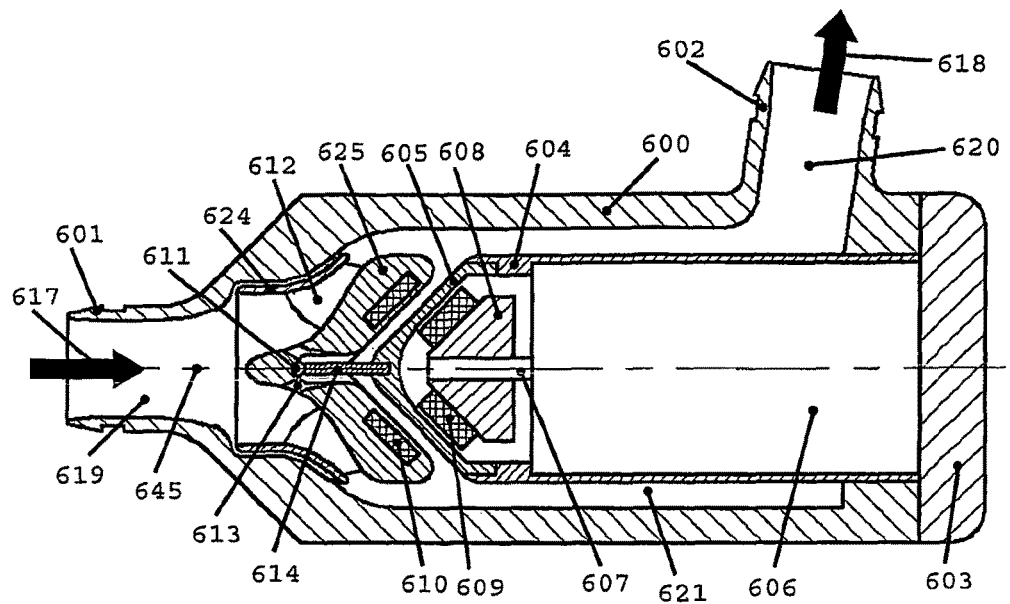
FIG. 22 is a cut-away view of a blood pump with a mechanical-magnetic rotor bearing in which the magnetic bearing is integrated into the diagonal coupling according to an exemplary embodiment of the present invention.

However, when it comes to implantable applications, blood pumps with an electromagnetic drive are the more suitable variant and they will be explained in greater detail below with reference to FIGS. 1 and 2. The drive unit (5, 6, 7, 8, 9) consists essentially of an electric motor (5) as well as of a coupling device (8, 9) that is needed to transfer the rotational movements of the motor (5) to the pump impeller (12). Electromagnetic drives (electromagnetic coupling) as well as electric motors with a permanent magnetic coupling will be considered within the scope of an exemplary embodiment of the present invention. A blood pump having a permanent magnetic coupling according to the present invention is shown, for example, in FIGS. 1 and 9. A blood pump having an electromagnetic coupling can be seen, for example, in FIG. 3 and FIG. 13. Depending on the direction of action of the coupling (axial, radial, diagonal), an exemplary embodiment of the present invention makes use of the forces and moments that act in the coupling device in order to stabilize the impeller in the pump housing and thus to provide a bearing for the rotor. A magnetic coupling that acts axially can be seen, for example in FIG. 1. In an axial coupling, the magnetic attractive forces act in the axial direction between the driving magnets (9) and the driven magnets (11). A magnetic coupling that acts radially is shown, for example, in FIG. 5. Here, the magnetic attractive forces in the coupling device (140, 136) act in the radial direction. In the case of a magnetic coupling that acts diagonally, as shown, for instance, in FIG. 22, the magnetic attractive forces act in a diagonal direction (axial and radial mixed form) between the driving magnets (609) and the driven magnets (610).

An exemplary embodiment of the present invention also comprises a flat design of the blood pump that is suitable for subcutaneous implantation, wherein the pump housing is configured in such a way that the space available is effectively utilized by the drive unit. Moreover, within the scope of an exemplary embodiment of the present invention, blood pumps are presented that use an oxygen-driven turbine as a drive system, thus providing an easily produced blood pump system, especially for short-term to medium-term applications.

Pump Impeller:
The pump impeller essentially serves to convert rotational energy that has been supplied to it via the coupling into hydraulic energy for purposes of building up pressure and flow which, by the same token, is the main function of the blood pump. Blade impellers as well as rotating elements that convey viscous substances can be employed as impellers in blood pumps. Since exemplary embodiments of the present invention employ impellers with blades, the term impeller is to be understood below to include blade impellers. Depending on the flow direction inside the impeller blades, a distinction is made between axial, radial and diagonal impellers. An exemplary embodiment of the present invention deals primarily with radial and diagonal impellers. The structure and mode of operation of the impeller will be explained in greater detail by way of an example with reference to FIGS. 1 and 2.

Figure 11:
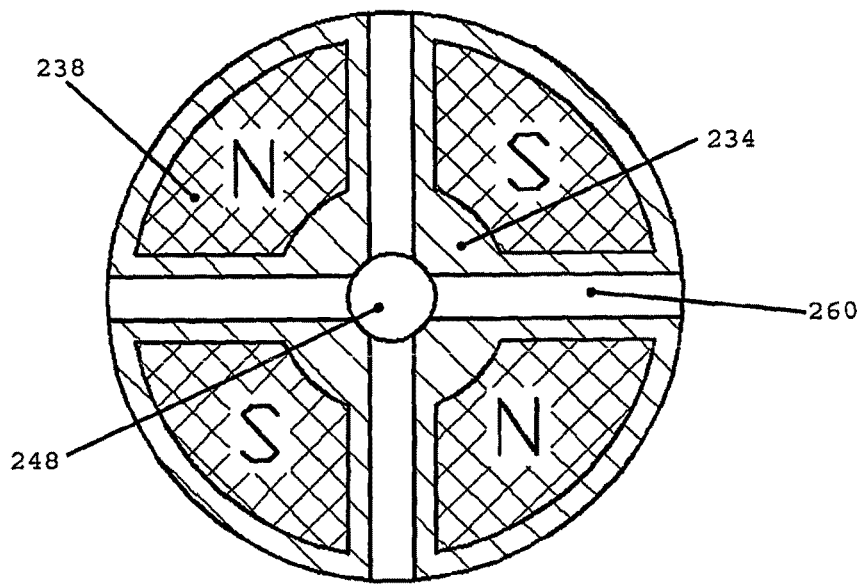
FIG. 11 is a cross-section view through the impeller of FIG. 9.

The pump impeller (12) is a rotating element fitted with blades (13) which can turn around its rotational axis (23). The transfer of the moments from the drive to the impeller (12) in the blood pump takes place electromagnetically by the electric motor (5) and by the magnetic coupling (8, 9) attached to the motor shaft (6). For this purpose, an even number of alternatingly polarized magnet segments (9) are attached to the pole shoe (8) on the driving side, said magnet segments (9) being located in a magnetically attractive orientation opposite from the magnet segments (11) located in the impeller (12) on the driven side (see FIG. 11). Owing to the attractive forces between the driven magnets (11) and the driving magnets (9), the rotational movements of the motor (5) are transferred to the impeller (12). The rotation of the impeller (12) in the pump housing (1) is likewise the reason for the flow and pressure build-up in the blood pump.

Depending on the clinical application and size of the pump, the rotational speed of the impeller (12) is between 2000 min$^{-1}$ and 20,000 min$^{-1}$. Here, the blood pump conveys a volume flow between 0.5 L/min and 10 L/min, depending on the physiological requirements, thus yielding a physiological pressure build-up between 0 mmHg and 800 mmHg. A blood flow of approximately 5 L/min at a physiological pressure build-up of 100 mmHg is needed to provide complete relief for the heart of a patient suffering from cardiac insufficiency. The flow and pressure build-up in the blood pump is based on the centrifugal effects of the rotating impeller (12) in the pump housing (1). Aside from the main conveying flow (34), a number of secondary flows are created which are of great significance when it comes to conveyance in a manner that is gentle on the blood, and this will be elaborated upon below.

Flow Pattern:

The term flow pattern refers here primarily to the blood flow through the pump.

For blood pumps, the requirements regarding a hematologically favorable flow pattern inside the pump generally apply, and these are characterized by:
avoiding high shear stress in the flow (→risk of hemolysis),
avoiding fluid temperatures that are too high (<42° C. [107.6° F.]) and flow rates that are too low (→risk of clotting or thrombi),
avoiding stalling and recirculation of the flow (→risk of thrombi or hemolysis),
minimizing blood contact with foreign surfaces (material-induced thrombocyte activation or risk of thrombi).

The flow pattern inside the blood pump will be explained in greater detail below with reference to FIGS. 1 and 2. The flow pattern inside the blood pump can be basically divided into main flow and secondary flows. The main flow (34) is the flow that runs via the pump inlet (2) into the pump, is then fed to the impeller (12) via a feed channel (14) that connects the pump inlet (2) to the impeller (12) and from there, it is imparted with a swirl by the rotation of the blades of the impeller (12) and then conveyed, finally leaving the pump again via the pump outlet (3) through a flow channel (15) associated with the impeller area. In this context, the pump inlet (2) is connected to the suction vessels (left ventricle or left atrium) of the patient, whereas the blood flow (22) exiting via the pump outlet (3) is conveyed via appropriate connection lines (cannulas, grafts) to the aorta (main artery) of the patient. The term secondary flows refers to all forms of flow in the blood pump that branch off from the main flow (34) and from there, run through other spaces of the pump. Especially the pressure distribution at the impeller (12), characterized by the higher pressure at the impeller outlet (40) in comparison to the pressure at the impeller inlet (41), gives rise to several secondary flows (35, 39, 42) that play a central role within the scope of the present invention.

For example, due to the higher pressure at the impeller outlet (40), fluid flows in a retrograde manner relative to the direction of the main flow (34), from the entrance of the gap space (37) to the low-pressure end (38) of the gap space (32) located opposite from it through the radial gap (32) between the impeller (5, 18) and the pump housing (1), thus causing a leakage flow (35). Here, the leakage flow (35) is separated from the main flow (34) by a shroud (18) that has been adapted to the outer rim of the blade contour, said shroud being permanently joined to the impeller blades. The special features of the leakage flow (35) and its fluid-mechanical interactions with the shroud (18) in terms of the inventive novelty will be elaborated upon below.

The axial gap (13) between the rear of the impeller (5) and the stationary pump element (10) located opposite from it creates another gap space (31) which, with an eye towards conveying the blood in a gentle manner, should be designed free of any flow stagnation.

Figure 2:
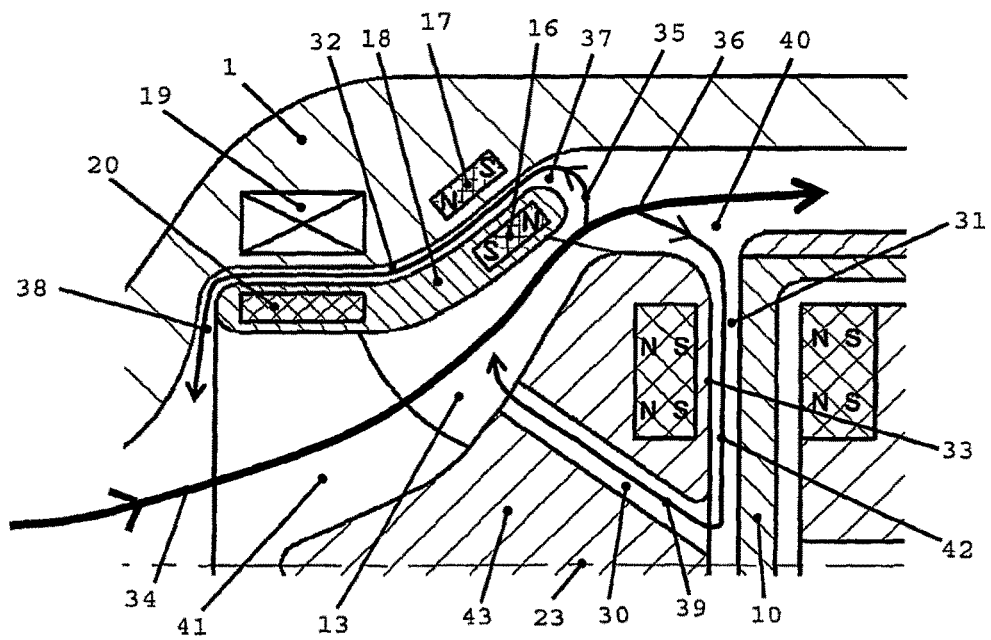
FIG. 2 is a cut-away view showing details of a flow pattern of the blood pump shown in FIG. 1, according to an exemplary embodiment of the present invention.

One possibility for washing out the axial gap space (31) is shown in FIGS. 1 and 2. A certain number (preferably 2 or 4) of rinsing channels (30) is created in the impeller body (43) in such a way that, owing to the pressure distribution at the impeller, a rinsing flow (39, 42) is induced from the high-pressure zone at the impeller outlet (40) to the low-pressure zone at the front of the impeller (41), said flow running radially inwards through the axial gap space (31) at the rear of the impeller (33), from where it is guided back into the main flow (34) via the rinsing channels (30). The use of this flow, particularly in terms of inventive novelty, will be elaborated upon below in conjunction with the mode of operation of the rotor bearing.

Figure 9:
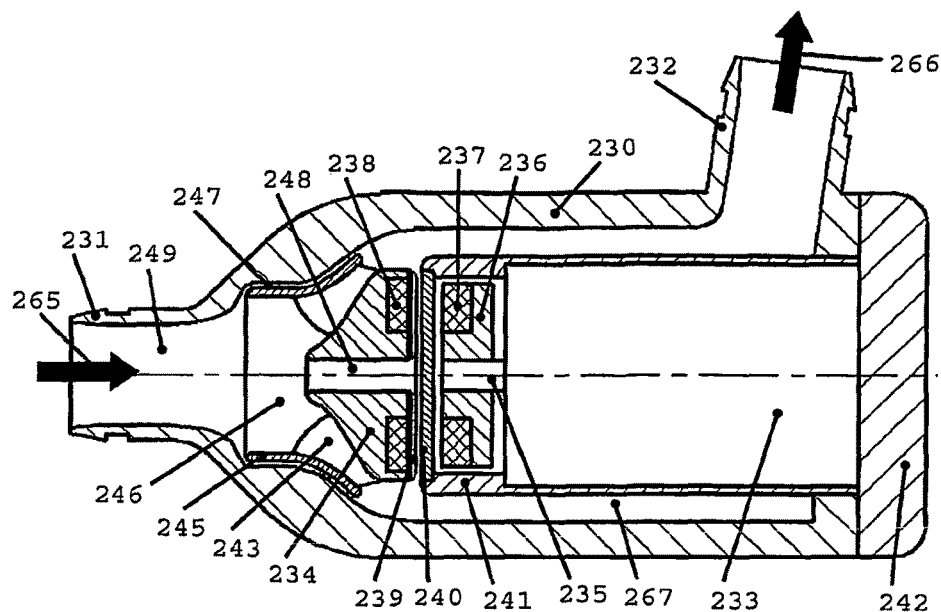
FIG. 9 is a cut-away view of a blood pump with a fluid-mechanical rotor bearing in which an integrated electric motor with a permanent magnetic axial coupling is employed as the drive according to an exemplary embodiment of the present invention.
Figure 10:
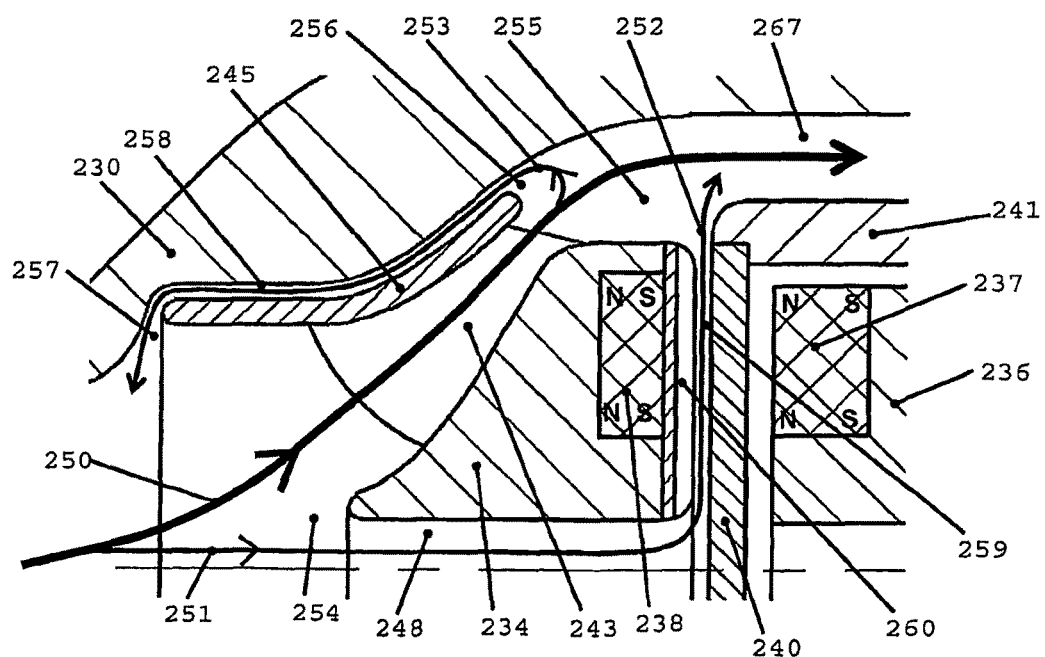
FIG. 10 is a cut-away view showing details of a flow pattern of the blood pump shown in FIG. 9 according to an exemplary embodiment of the present invention.

Another variant for washing out the critical rear of the impeller consists of the configuration of the pump according to FIGS. 9 and 10, whereby a central rinsing channel (248) created in the impeller hub (234) as well as a secondary set of blades (260) provided at the rear of the impeller induce another centrifugal flow (252) in such a manner that, due to the centrifugal forces that act in the secondary set of blades (260), a portion of the main flow (250) is branched off as rinsing flow (251, 252) via the rinsing channel (248) and is conveyed in the side space (259) radially towards the outside until the rinsing flow (252) finally once again enters the main flow (250) in the high-pressure zone at the impeller outlet (255). The special aspects of this rinsing flow (251, 252) as well as its significance for the inventive novelty regarding the bearing of the impeller (234) will be elaborated upon below in conjunction with the rotor bearing.

An exemplary embodiment of the present invention relates to a blood pump that is suitable for conveying blood in extracorporeal and intracorporeal circulation systems over short-term to medium-term periods of use (from a few hours to several months) as well as over long periods of use (several months to several years). This objective is achieved in an exemplary embodiment of the present invention by a rotary blood pump having a hemocompatible rotor bearing that remains stable over the long term.

For long-term use in which the blood pump has to be implanted into the patient, two rotor bearing concepts are presented within the scope of the present invention, in which the pump impeller is mounted on bearings in the pump housing in a manner that is completely contact-free and thus free of wear and tear. These concepts are:
1) blood pump with an electromagnetic radial bearing and a permanent magnetic axial bearing,
2) blood pump with a hydrostatic radial bearing and a hydrodynamic axial bearing.

For short-term to medium-term use for which extracorporeal placement of the blood pump is usually appropriate, a rotor bearing concept is presented within the scope of an exemplary embodiment of the present invention that is based on a combination of several bearing principles as a hybrid bearing. In particular, it is:
3) a blood pump with a mechanical-magnetic rotor bearing.

Likewise shown within the scope of an exemplary embodiment of the present invention are modifications of the individual variants which entail clinical as well as patient-relevant advantages and which also contribute to increasing operating reliability and to reducing the manufacturing effort.

It is practical to design the blood pump in such a way that it comprises at least two elements that are physically separated from each other, whereby at least one of the elements is configured such that it exerts axial restoring forces, whereby at least one other element provides a contact-free bearing and whereby the additional element is a fluid-mechanically stabilizing bearing and whereby the fluid-mechanical stabilization is based on an interaction between a shroud and the pump housing.

It is likewise practical to design the blood pump in such a manner that it comprises at least two elements that are physically separated from each other, whereby at least one of the elements is constructed in such a way that it has a fluid-mechanically stabilizing effect in a radial directional component and in that at least another element is a radial magnetic bearing.

It is also practical to configure the blood pump in such a way that it comprises at least two elements that are physically separated from each other, whereby at least one of the elements is constructed in such a way that it has a shroud that is designed such that it has a fluid-mechanically stabilizing effect in a radial directional component and at least another element constitutes a radial magnetic bearing.

FIGS. 1 to 8 relate to a blood pump according to an exemplary embodiment of the invention, with an electromagnetic radial bearing and a permanent magnetic axial bearing.

FIGS. 9 to 14 relate to a blood pump according to an exemplary embodiment of the invention, with a hydrostatic radial bearing and a hydrodynamic axial bearing.

FIGS. 15 to 31 relate to a blood pump according to an exemplary embodiment of the invention, with a mechanical-magnetic rotor bearing.

FIGS. 32 to 35 relate to a blood pump according to an exemplary embodiment of the invention, having a harmonious flat design of the blood pump.

Figure 36:
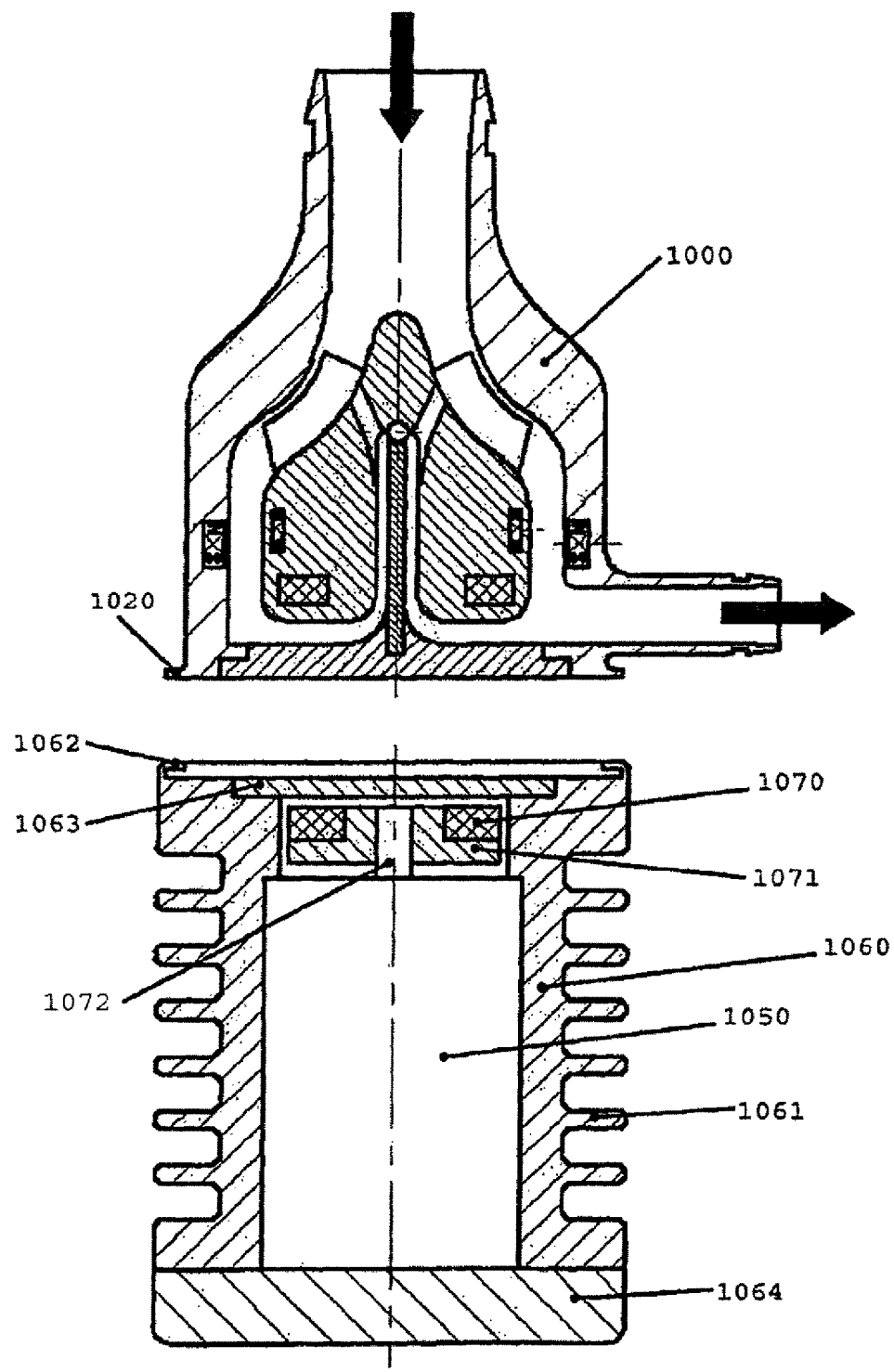
FIG. 36 is a cut-away view of blood pump with a separate drive unit, whereby the pump head is driven by an electric motor.

FIG. 36 relates to a blood pump according to an exemplary embodiment of the present invention (especially the mechanical-magnetic rotor bearing), whereby the blood pump is driven as a separable pump head by an external electric motor.

Figure 37:
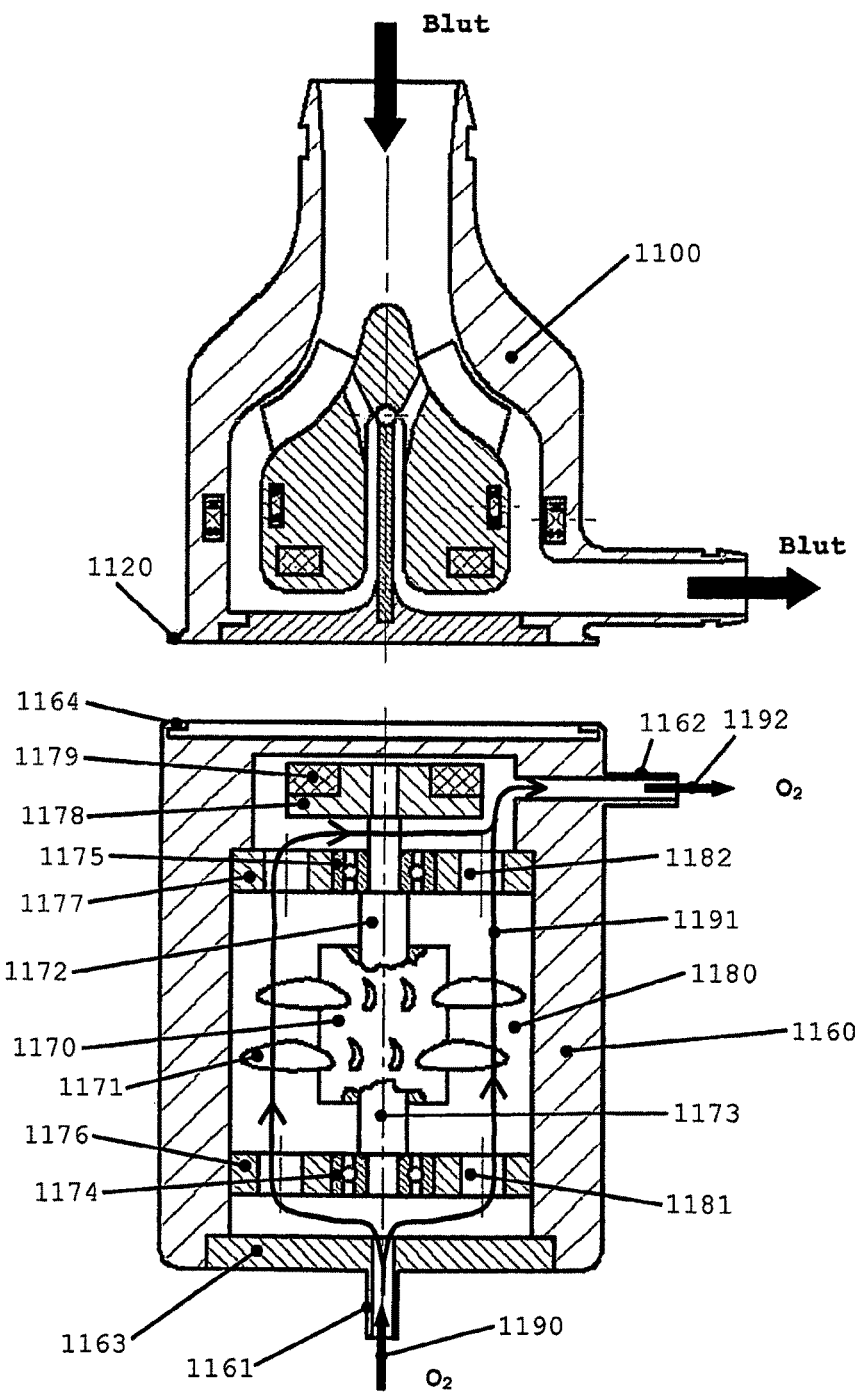
FIG. 37 is a cut-away view of a blood pump with a separate drive unit, whereby the pump head is driven by an oxygen-operated turbine.
Figure 38:
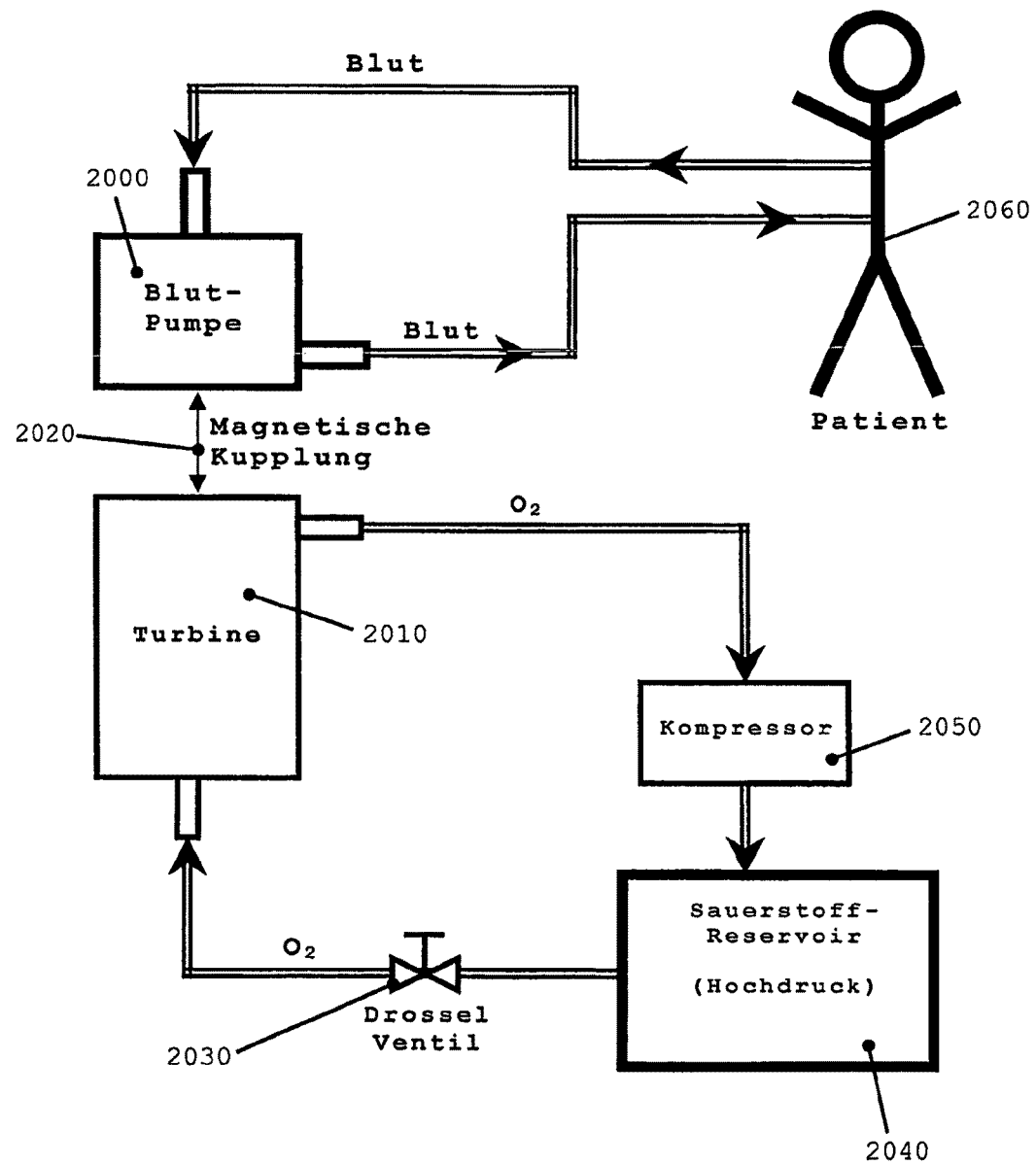
FIG. 38 is a diagram of the blood pump of FIG. 27 being used in a patient as a purely blood-conveying system (without oxygenator)
Figure 39:
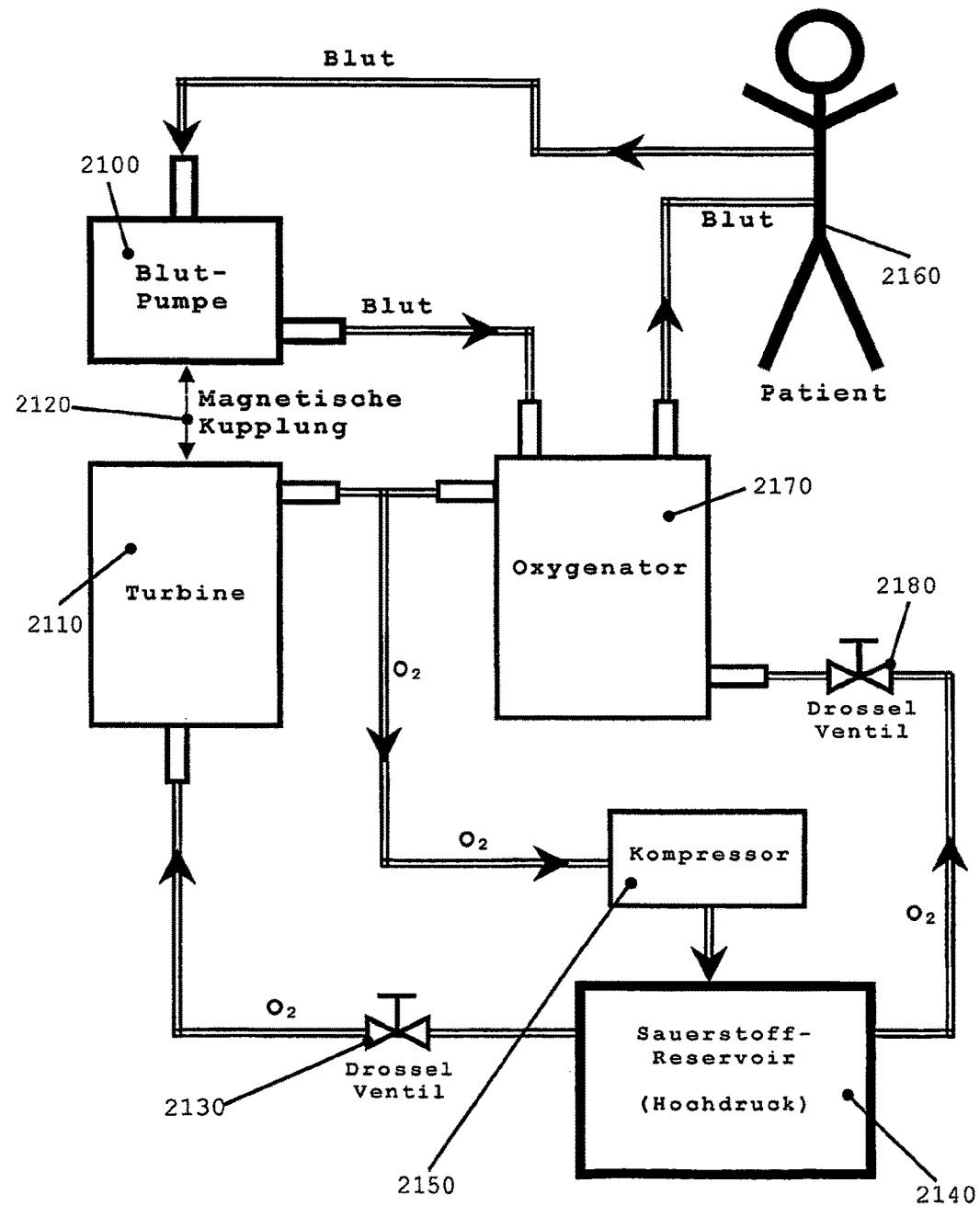
FIG. 39 is a diagram of the blood pump of FIG. 27, being used in a patient in combination with a blood-oxygenation system (oxygenator)

FIGS. 37 to 39 relate to a blood pump according to an exemplary embodiment of the invention, whereby the blood pump is driven as a separable pump head by an external turbine.

Figure 41:
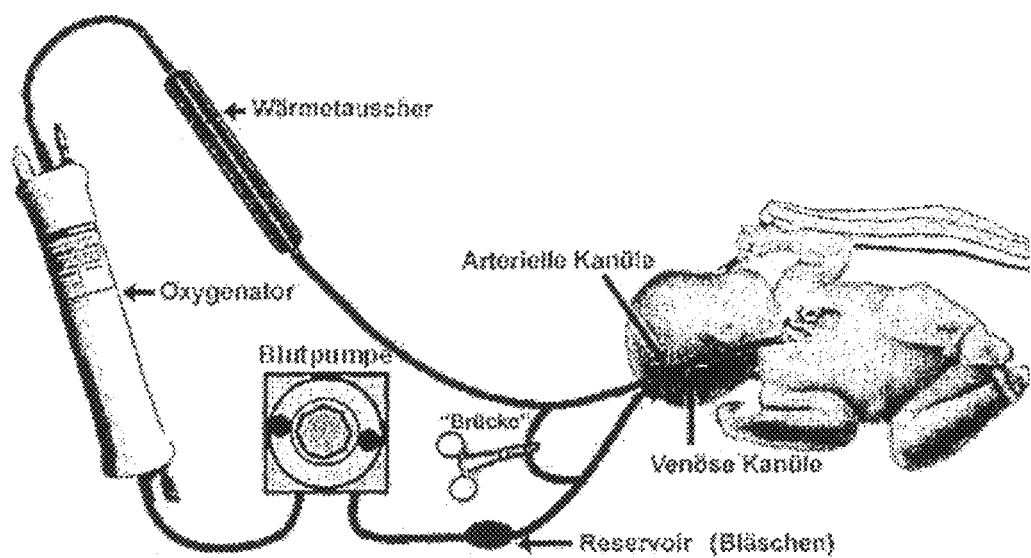
FIG. 41 is a diagram of an extracorporeal blood pump in the ECMO system.

FIGS. 40 to 41 relate to the general state of the art.

FIGS. 1 to 35 relate especially to long-term use (VAD, ECMO, etc.) in which the blood pump is designed so that it can be implanted, as illustrated by way of an example in FIG. 40.

FIGS. 36 to 39 relate especially to short-term to medium-term uses (HLM, ECMO, short-term VAD, etc.), in which the blood pump is placed extracorporeally.

FIGS. 1 and 2 show a blood pump in which the pump impeller (12) in the pump housing (1) is supported in the radial direction by an electromagnetic bearing (19, 20) and in the axial direction by a permanent magnetic bearing (16, 17). The impeller (12) is driven here by an electric motor (5) that is integrated into the pump housing (1), whereby the rotational movements of the motor (5) are transferred to the impeller (12) via a permanent magnetic axial coupling (8, 9, 11). The electric motor (5) is located in a motor housing (7) and is also hermetically sealed by the motor cover (10) vis-à-vis the space (15) through which blood flows.

The permanent magnetic coupling (8, 9) is connected on the drive side to the motor shaft (6) via the pole shoe (8) in a manner that is rotationally rigid. Here, the pole shoe (8) ensures the magnetic feedback of the individual driving magnets (9) and is made of a magnetically conductive material (for instance, magnetizable steel). The coupling magnets (9, 11) are permanent magnets that, in particular, are made of high-performance magnetic materials (rare earth magnets) such as, for example, neodymium-iron-boron (NdFeB) or samarium-cobalt (SmCo). On the driven side, the coupling magnets (11) are embedded in the pump impeller (12), and consequently, they do not come into contact with the medium being conveyed (blood), so that the risk of corrosion to the coupling magnets (11) in the blood flow can be ruled out. The two coupling halves (9, 11) each consist of an even number (preferably 2, 4, 6, or 8) of individual magnet segments that form a full circle when put together. The depiction in FIG. 11 serves as an illustration of this. Here, the individual magnet segments (11 or 238) are polarized alternatingly in the axial direction. On the drive side of the magnetic coupling (9), an equal number of magnet segments are present that are likewise polarized alternatingly in the axial direction. The driving magnets (9) are now arranged opposite from the driven magnets (11) in such a way that magnetic attractive forces act between them in the axial direction, as can be seen in FIG. 2. When the motor shaft (6) and thus the coupling half (8, 9) on the drive side execute rotational movements, the two coupling halves are turned with respect to each other until the air gap moment in the magnetic coupling (9, 11) matches the load moment on the impeller side (12), thus transferring the rotational movements from the motor (5) to the pump impeller (12). The restoring moment in the magnetic coupling (9, 11) is dimensioned in such a way that the load moments needed for operating the blood pump can be transferred without uncoupling. This is achieved particularly through the alternating polarization of the individual magnet segments and can be appropriately raised by increasing the number of poles of the coupling.

In this context, the electric motor (5) is a commercially available electric motor having an adequate service life (at least 6 months) and sufficient power (approximately 20 watts), so that the drive of the pump impeller (12) is ensured over the entire operating range (0 L/min to 7 L/min, 0 mmHg to 200 mmHg, 0 min$^{-1}$ to 10,000 min$^{-1}$) of the blood pump.

Therefore, during the operation of the blood pump, the pump impeller (12) executes rotational movements around its rotational axis (23), during which it has to be stabilized in the axial direction by means of a suitable rotor bearing in order to prevent the pump impeller (12) from knocking against the pump housing (1). In the axial direction, it is not only the magnetic attractive forces of the magnetic coupling (9, 11) that act upon the pump impeller (12), but also the hydraulic flow forces, albeit in the opposite direction (axial shear).

In an exemplary embodiment of the present invention as shown in FIGS. 1 and 2, the pump impeller (12) in the pump housing (1) is axially supported by a permanent magnetic axial bearing (16, 17). Here, the permanent magnetic axial bearing consists of a permanent magnetic device (17) (stator magnet) that is positioned immovably in the pump housing (1), as well as of another permanent magnetic device (16) (rotor magnet) that is integrated into the pump impeller (12) or into one of its parts such as, for example, the shroud (18) or the impeller blades (13), as a result of which said permanent magnetic device (16) executes the same rotational movements around the rotational axis (23) as the pump impeller itself. FIGS. 1 and 2 show a possibility for the configuration of the permanent magnetic axial bearing. Here, the stator magnet (17) and the rotor magnet (16) each consist of permanent magnetic rings that are oppositely polarized in the axial direction. In this case, the rotor magnet (16) is integrated into the shroud (18) and it is radially opposite from the stator magnet (17) in the pump housing. In the preferred embodiment of the blood pump, the radial air gap between the stator magnet (17) and the rotor magnet (16) amounts to between 0.1 mm and 5.0 mm, especially between 0.5 mm and 2.0 mm.

When the pump impeller (12) is axially deflected in the pump housing (1), permanent magnetic forces occur between the stator magnet (17) and the rotor magnet (16) which then axially restore the position of the pump impeller (12) in the pump housing (1). The axial deflection of the pump impeller (12) in the pump housing (1) is limited by means of such an axial bearing in such a way that axial contact of the pump impeller (12) and of its individual parts, such as the shroud (18) and impeller blades (13), with the pump housing (1) or with other stationary pump elements (10) is prevented over the entire operating range of the blood pump. In an exemplary embodiment of the present invention, this is achieved by using high-performance magnets (rare earth magnets) such as, for instance, NdFeB or SmCo as the materials for the permanent magnetic axial bearing (16, 17), whose magnetic restoring force is of a greater magnitude in case of axial deflections of the pump impeller (12) in the pump housing (1) in the axial direction than the axial attractive force that acts in the magnetic coupling (9, 11). Since the permanent magnetic axial bearing (16, 17) can be alternately loaded in the axial direction, this ensures that the hydraulic flow force (axial shear) that acts opposite to the coupling force is absorbed by the magnetic bearing (16, 17). The axial deflections of the pump impeller (12) that occur during the operation of the pump amount to between 0 mm and 5.0 mm, especially between 0.01 mm and 1.0 mm.

Aside from being subjected to the axial restoring forces, the permanent magnetic axial bearing (16, 17) at the same time experiences unstable radial attractive forces that rise steadily as the radial deflection of the pump impeller (12) in the pump housing (1) increases, and said forces have to be stabilized by means of another radial bearing.

In an exemplary embodiment of the present invention, the radial bearing of the pump impeller (12) in the pump housing (1) is made possible by an additional electromagnetic bearing (19, 20) that is physically separated from the electromagnetic drive (5, 6, 8, 9). Such a separation of the electromagnetic bearing (19, 20) from the electromagnetic drive (5, 6, 8, 9) in an exemplary embodiment of the present invention entails the considerable advantage that the drive of the pump impeller (12) is maintained during malfunctions or failure of the electromagnetic bearing (19, 20), so that the blood pump can be further operated under emergency conditions without any hemodynamic impairment for the patient. Moreover, such a configuration of the electromagnetic rotor bearing and electromagnetic drive has the advantage that the drive unit and thus the entire blood pump can have a much more compact design, which greatly facilitates the implantation of the blood pump.

The electromagnetic radial bearing (19, 20) consists of a stator device (19) and of a rotor device (20) between which, during radial deflections of the pump impeller (12) in the pump housing (1), electromagnetic forces occur in the radial direction in such a way as to prevent radial contact of the pump impeller (12) and of its individual components (13, 18) with the pump housing (1). In an exemplary embodiment of the present invention, this is made possible by an electromagnetic stator device (19) as well as another permanent magnetic rotor device (20). The magnetic rotor device (20) is integrated into the pump impeller (12) or into one of its parts such as the shroud (18) or the impeller blades (13), thus executing the same rotational movements around the rotational axis (23) as the pump impeller (12) itself. One possibility to configure the electromagnetic radial bearing (19, 20) is to use permanent magnets or magnetizable materials for the rotor device (20). The stator device (20), in contrast, consists of a certain number (preferably 1 to 5, particularly 2 to 3) of regulated electromagnets that are integrated into the pump housing (1) and distributed in circumferential direction. The radial distance between the pump impeller (12) and the pump housing (1) or between the rotor device (20) and the pump housing (1) is detected by displacement measuring sensors (for example, inductive sensors, capacitive sensors, optical sensors or ultrasound sensors) that are installed in the stator device (19) or in the pump housing (1). During radial deflections of the impeller (12) in the pump housing (1), the measured signal serves to activate the electromagnets in the stator device (19) in such a manner that electromagnetic forces between the stator device (19) and the rotor device (20) are active in the radial direction, said forces restoring the pump impeller (12) to a concentric position in the pump housing (1).

In an exemplary embodiment of the present invention, an embodiment of the blood pump also relates to uniting the permanent magnetic axial bearing (16, 17) and the electromagnetic radial bearing (19, 20) into one unit that, in its entirety, remains physically separated from the electromagnetic drive (5, 6, 8, 9), thus retaining the above-mentioned advantages of the physical separation between the rotor bearing and the pump drive. Uniting the electromagnetic radial bearing with the permanent magnetic axial bearing also entails the advantage that, under certain circumstances, the entire rotor bearing and thus also the blood pump can have a more compact design, thus being more suitable for implantation.

Certain measures have been taken within the scope of an exemplary embodiment of the present invention in conjunction with the emergency operation properties of the blood pump having such a rotor bearing and these measures will be explained in greater detail below. Since the rotor bearing has a permanent magnetic axial bearing (16, 17) in the axial direction, and since it is maintenance-free and the permanent magnets have an unlimited service life, there is no need for any additional safety measure in order to maintain the axial rotor stability. However, when it comes to the bearing of the pump impeller (12) in the radial direction, measures have to be taken to ensure stabilization of the impeller (12) in the pump housing (1), even during malfunctions or failure of the electromagnetic radial bearing.

For this purpose, an exemplary embodiment of the present invention provides for a fluid-mechanical radial bearing whose mode of operation can be seen in FIG. 2. The radial gap between the shroud (18) and the pump housing (1) located opposite from it creates a flow space (32) through which, due to the above-described pressure distribution at the impeller (12), a leakage flow (35) runs in a retrograde manner relative to the direction of the main flow. The cause of this leakage flow (35) that runs primarily in the axial direction is, as already mentioned above, the hydrostatic pressure differential between the entrance (37) and the exit (38) of the gap space (32). When the pump impeller (12) is in a concentric position in the pump housing (1), there is a constant pressure distribution in the gap space (32) in the circumferential direction, so that no radial forces act on the shroud (18) or on the pump impeller (12). However, during radial deflections of the impeller (12) in the pump housing (1), the pressure distribution changes in the now eccentric gap space (32) in the circumferential direction in such a way that the hydrostatic pressure in the narrower gap area becomes greater than the hydrostatic pressure in the enlarged gap area that lies diametrically opposed thereto, resulting in a radial restoring force on the shroud (18) and thus also on the pump impeller (12), which once again puts the impeller into the concentric position in the pump housing ("Lomakin effect").

Furthermore, owing to the rotational movement of the impeller (12), a rotational flow is created in the gap space (32), which gives rise to a hydrodynamic radial bearing ("Reynolds effect") during radial deflections of the impeller (12) in the pump housing (1).

In this manner, it is ensured that, even in case of failure of the electromagnetic radial bearing (19, 20), the pump impeller (12) remains supported contact-free in the pump housing (1). The use of the fluid-mechanical radial bearing resulting from the failure of the electromagnetic radial bearing (19, 20)—due to the radial attractive forces of the permanent magnetic axial bearing (16, 17) that continue to exist—is characterized by an operating behavior in which, due to the eccentric position of the pump impeller (12) in the pump housing (1), a locally constricted gap space (32) is created between the shroud (18) and the pump housing (1). The resultant increased shear stress on the blood flow as well as the associated hemolysis have to be accepted during the period of the emergency operation.

Figure 3:
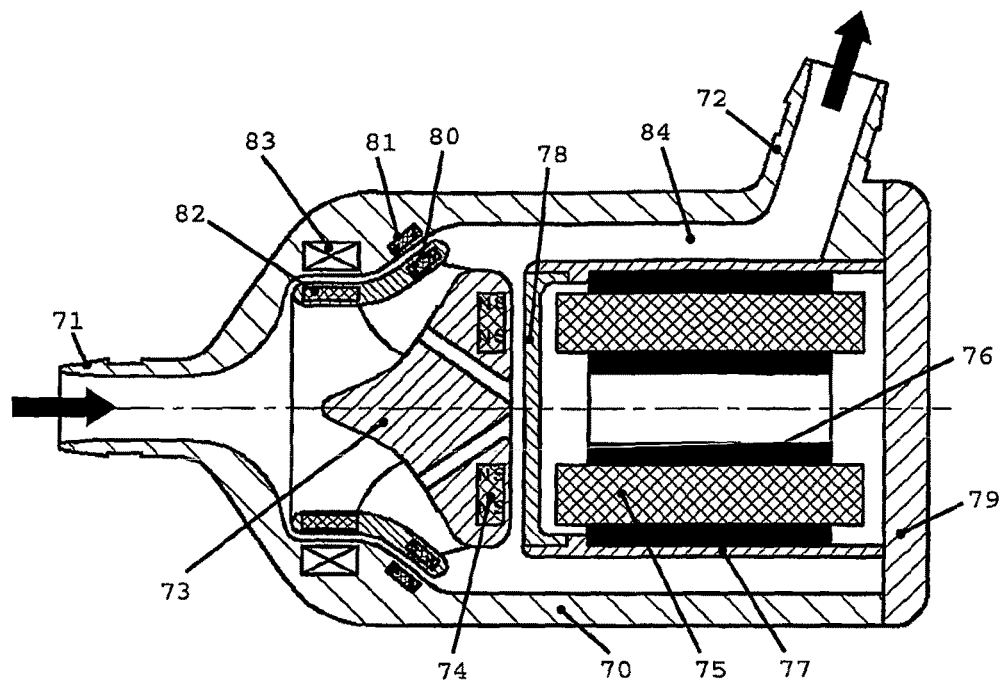
FIG. 3 is a cut-away view of a blood pump with an electromagnetic rotor bearing in which an integrated electric motor with an electromagnetic axial coupling is employed as the drive according to an exemplary embodiment of the present invention.

FIG. 3 shows a blood pump in which the rotor bearing and the flow pattern inside the blood pump have the same structure and the same mode of operation as in the blood pump shown in FIGS. 1 and 2. FIG. 3, however, shows an exemplary embodiment of the blood pump in which the integrated drive (75, 76, 77, 78) is not driven by a permanent magnetic coupling, but rather, by an electromagnetic axial coupling (75, 76). The advantages of such an exemplary embodiment are, on the one hand, the reduction in the number of components and thus a lessening of the complexity of the blood pump and, on the other hand, the longer service life of the drive according to FIG. 3, since here, the pump impeller (73) is not driven by an additional electric motor (with its limited service life due to the roller bearings used in it), but rather, directly by an electromagnetic coupling (75, 76). According to the general state of the art, an electromagnetic coupling is based on an electromagnetic rotating field that is transferred contact-free from the electromagnets (75, 76) to the coupling magnets (74) on the driven side in the pump impeller (73). The further mode of operation of the blood pump, especially of the electromagnetic axial bearing (80, 81) as well as of the electromagnetic radial bearing (82, 83) of the pump impeller (73) in the pump housing (70), is analogous to that of the embodiment of the blood pump according to FIGS. 1 and 2.

Figure 4:
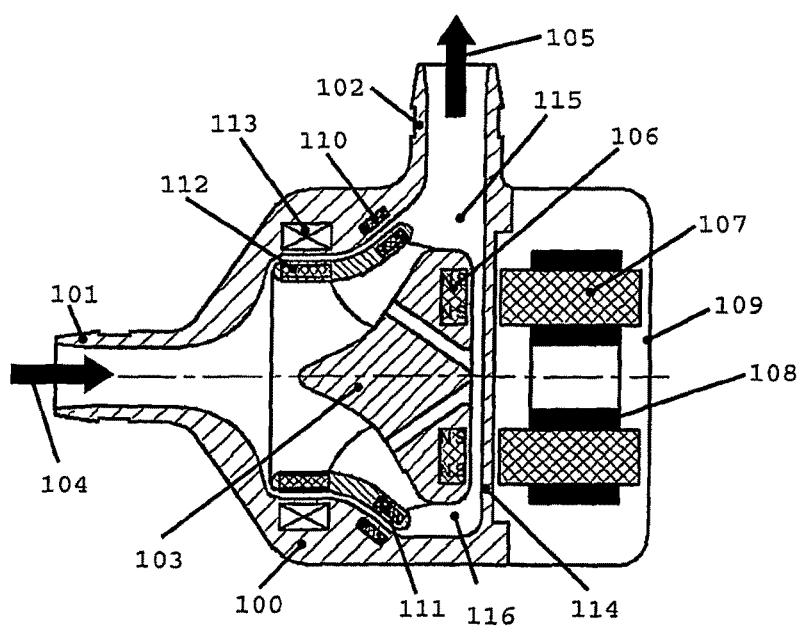
FIG. 4 is a cut-away view of a blood pump with an electromagnetic rotor bearing in which an external electric motor with an electromagnetic axial coupling is employed as the drive according to an exemplary embodiment of the present invention.

FIG. 4 shows a blood pump that has the same structure and the same mode of operation as the blood pump in FIG. 3. In FIG. 4, however, the exemplary embodiment of the blood pump is such that the electromagnetic drive (107, 108, 109) is not integrated into the interior of the pump housing (100), but rather, is attached outside of it at the rear of the pump housing (114). The advantages of such a configuration are the more compact design of the pump housing (100) and thus conceivably even of the entire blood pump, as a result of which it lends itself to be implanted and the contact of the blood flow with foreign surfaces can be minimized. Since the axial dimensions of the pump housing (100) are substantially reduced, this embodiment offers the additional possibility of positioning the pump outlet (102) closer to the impeller area (115, 116) and of employing the radial impeller shape in addition to the diagonal impeller shape for the design of the pump impeller (103). The advantages of a radial impeller shape in comparison to a diagonal impeller shape, as can be seen in the embodiments of FIGS. 1 and 3, are that, with radial impellers, the rotational speed of the impeller during operation of the blood pump is lower than that of the diagonal impeller shape because of the more pronounced centrifugal effects. Lowering the impeller rotational speed not only translates into less stress on the individual components of the blood pump, but especially entails the advantage that the shear stresses on the blood and thus the hemolysis rate can be reduced.

The mode of operation of the electromagnetic axial coupling (106, 107, 108) matches that of the coupling device of FIG. 3.

The further mode of operation of the blood pump, especially of the permanent magnetic axial bearing (110, 111) as well as of the electromagnetic radial bearing (112, 113) of the pump impeller (103) in the pump housing (100), is analogous to that of the exemplary embodiment of the blood pump of FIGS. 1 and 3.

Figure 5:
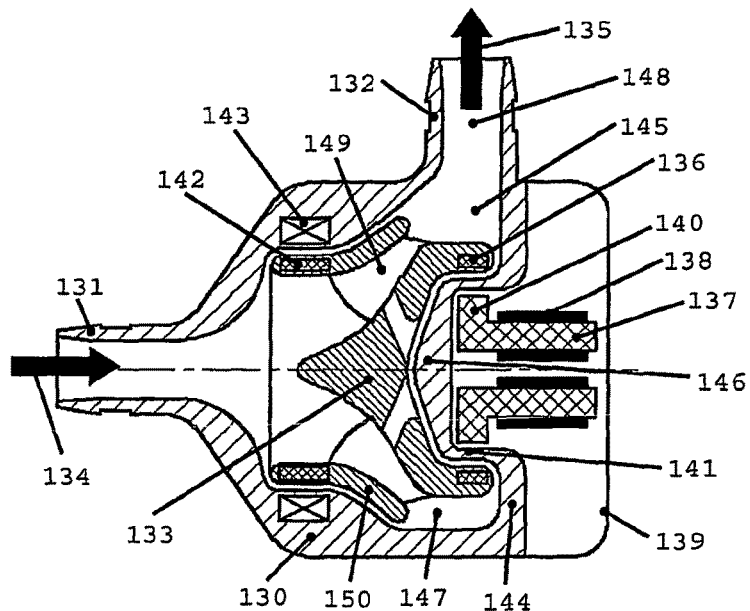
FIG. 5 is a cut-away view of a blood pump with an electromagnetic rotor bearing in which an external electric motor with an electromagnetic radial coupling is employed as the drive according to an exemplary embodiment of the present invention.
Figure 6:
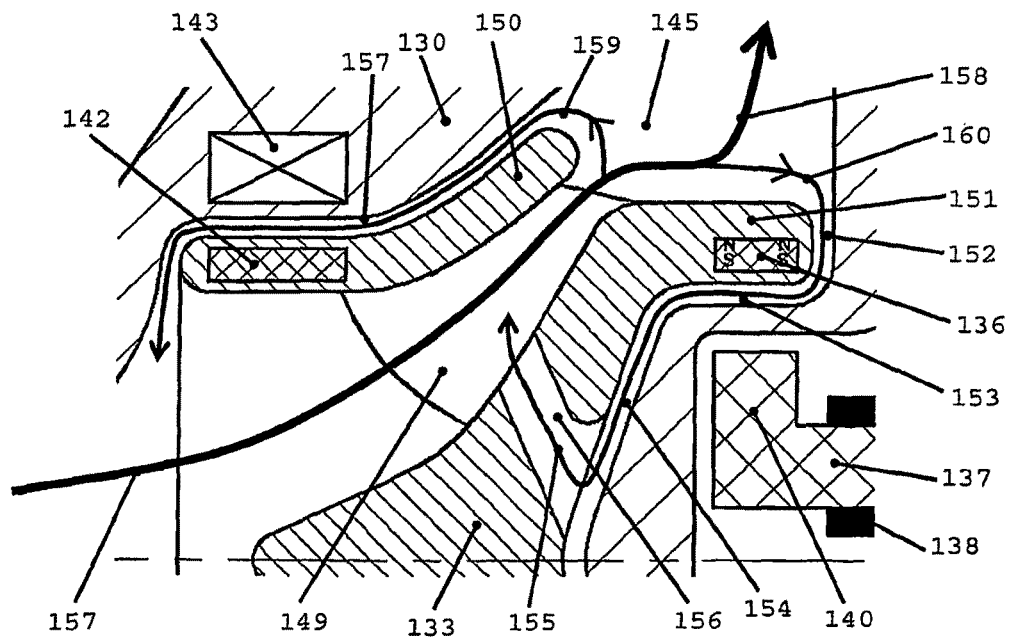
FIG. 6 is a cut-away view showing details of a flow pattern of the blood pump shown in FIG. 5, according to an exemplary embodiment of the present invention.

FIGS. 5 and 6 show a blood pump in which the pump impeller (113) is driven by an electromagnetic coupling (136, 137, 138, 140) that acts radially. The pump impeller (133) in the pump housing (130) is supported in the radial direction by an electromagnetic bearing (142, 143) analogously to the embodiments of the blood pump of FIGS. 1, 3 and 4. However, the impeller (133) in the exemplary embodiment according to FIGS. 5 and 6 is supported in the axial direction by means of a magnetic axial bearing that is already implemented in the radial coupling (136, 140). In the case of axial deflections of the impeller magnets (136) with respect to the driving magnets (140), a magnetic coupling (136, 140) that acts radially will be subjected to an axial restoring effect that strives to bring the driving magnets (136) and thus also the pump impeller (133) back to the axial state of balance. Consequently, the magnetic coupling that acts radially is a magnetic axial bearing.

Therefore, the essential advantage of such a blood pump having a magnetic coupling that acts radially is that no additional axial bearing is needed to stabilize the pump impeller (133) in the pump housing, so that the entire blood pump can have a much more compact design and can be manufactured more easily. Regarding the placement of the drive unit (137, 138, 139, 140), the same advantages apply as in the case of the exemplary embodiment of the blood pump according to FIG. 4. When it comes to the physical separation of the electromagnetic bearing (142, 143) from the electromagnetic drive (137, 138, 139, 140), the same advantages apply as in the case of the exemplary embodiment of the blood pump according to FIGS. 1, 3 and 4. Concerning the fluid-mechanical rotor bearing in the flow gap (157) between the shroud (150) and the pump housing (130) located opposite from it, in case of failure of the electromagnetic bearing (142, 143), the same explanations and advantages apply as in the exemplary embodiment of the blood pump according to FIG. 1.

As far as the flow pattern inside the blood pump is concerned, additional special features are present in the exemplary embodiment according to FIG. 5, and these will be explained in greater detail with reference to FIG. 6. Due to the radial direction of action of the magnetic coupling (136, 140), a changed flow pattern arises at the rear of the impeller (133), and this flow pattern is crucial in terms of the radial stabilization of the pump impeller (133) in case of failure of the electromagnetic radial bearing (142, 143) and of the resulting emergency operation of the blood pump.

The gap spaces (152, 153, 154) between the rear of the pump impeller (133) and the areas of the pump housing (141, 144, 146) that are opposite from it form a flow space through which fluid flows in a retrograde manner relative to the direction of the main flow (157), from the high-pressure zone at the impeller outlet (145) through the individual gap spaces (152, 153, 154) as well as through the rinsing channels (156) created in the impeller body (133) towards the front of the impeller (133) as a result of the above-mentioned pressure distribution at the impeller (133). This rinsing flow (160, 155), on the one hand, ensures that flow stagnations in the individual flow zones (152, 153, 154, 155, 156) are avoided, thus reducing the risk of thrombi in the blood pump. On the other hand, especially the flow through the gap space (153) provides a fluid-mechanical rotor bearing that becomes effective in case of failure of the electromagnetic radial bearing (142, 143), said fluid-mechanical rotor bearing stabilizing the impeller (133) in the radial direction during radial deflections of the pump impeller (133) in the pump housing (130) in the manner already explained in conjunction with the fluid-mechanical rotor bearing of FIG. 1 or 2. Therefore, with the exemplary embodiment of the blood pump according to FIGS. 5 and 6, an additional emergency-operation bearing (153, 160) is provided which altogether contributes to enhancing the operating reliability of the blood pump.

The further mode of operation of the blood pump, especially that of the electromagnetic radial bearing (142, 143) of the pump impeller (133) in the pump housing (130), is analogous to that of the exemplary embodiment of the blood pump according to FIGS. 1, 3 and 4.

Figure 7:
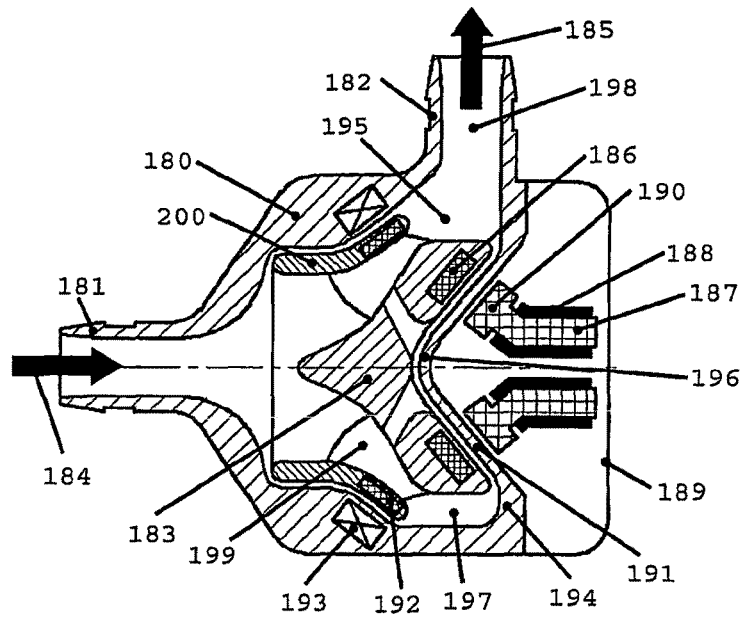
FIG. 7 is a cut-away view of a blood pump with an electromagnetic rotor bearing in which an external electric motor with an electromagnetic diagonal coupling is employed as the drive according to an exemplary embodiment of the present invention.
Figure 8:
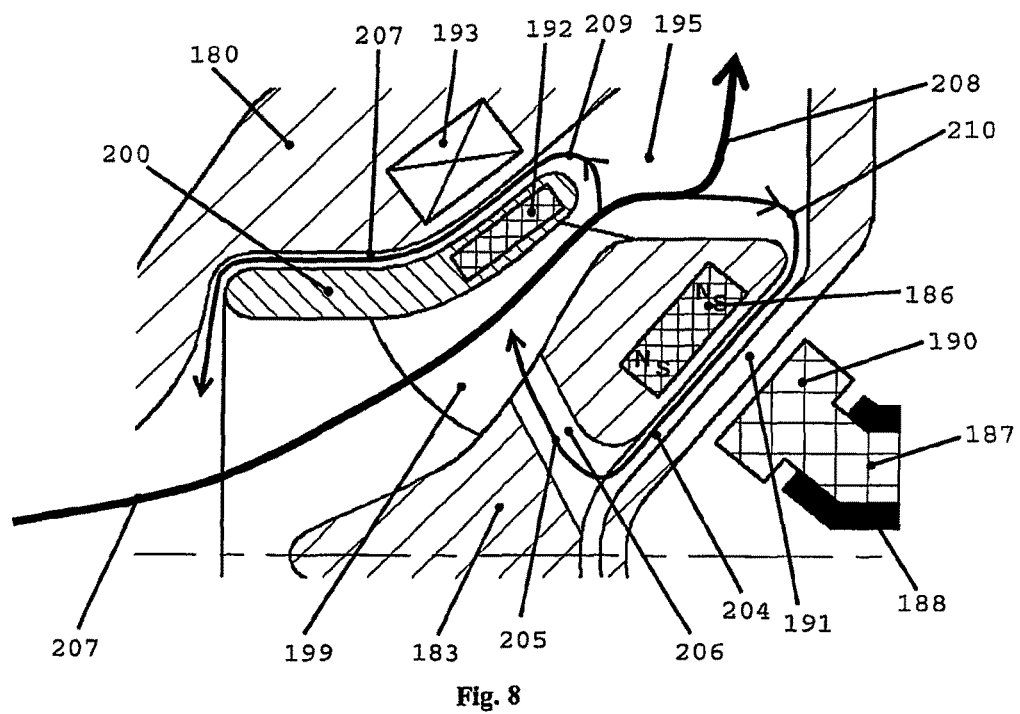
FIG. 8 is a cut-away view showing details of a flow pattern of the blood pump shown in FIG. 7 according to an exemplary embodiment of the present invention.

FIGS. 7 and 8 show a blood pump in which the pump impeller (183) is driven by an electromagnetic coupling (186, 187, 188, 189, 190) that acts diagonally. Here, the pump impeller (183) is likewise supported in the diagonal direction and, unlike in the preceding exemplary embodiments of the blood pump, the radial bearing and the axial bearing of the impeller (183) here are combined into one unit, whereby the electromagnetic restoring forces in the magnetic bearing (192, 193), depending on the deflection of the impeller (183) in the pump housing (180), have an appertaining component in the axial direction as well as another component in the radial direction. Since the direction of action of the electromagnetic stator device (193) runs in the diagonal direction, the orientation of the rotor device (192) is such that it is likewise active in the diagonal direction in a preferred exemplary embodiment of the blood pump. Since the electromagnetic attractive forces in the magnetic coupling (186, 190) likewise run in a diagonal direction, these attractive forces will already cause a radial centering of the impeller (183) in the pump housing (180) at sufficiently small operating tolerances, so that the electromagnetic rotor bearing (192, 193) takes on primarily the function of an axial bearing. Only in the case of unexpected external impact forces (for example, if the patient falls) will the magnetic bearing (192, 103) likewise become active in the radial direction.

The essential advantage of such an exemplary embodiment lies in the more compact design of the rotor bearing and, as a result, in the compactness of the entire blood pump, which entails considerable advantages for the surgery during the implantation procedure.

Regarding the placement of the drive unit (187, 188, 189, 190), the same advantages apply as in the case of the exemplary embodiment of the blood pump according to FIGS. 4 and 5. When it comes to the physical separation of the electromagnetic bearing (192, 193) from the electromagnetic drive (187, 188, 189, 190), the same advantages apply as in the case of the exemplary embodiment of the blood pump according to FIGS. 1, 3, 4 and 5. Concerning the fluid-mechanical rotor bearing in the flow gap (207) between the shroud (200) and the pump housing (180) located opposite from it, in case of failure of the electromagnetic bearing (192, 193), the same explanations and advantages apply as in the exemplary embodiment of the blood pump according to FIG. 1.

As far as the flow pattern inside the blood pump is concerned, however, additional special features are present in the exemplary embodiment according to FIG. 7, and these will be explained in greater detail with reference to FIG. 8. Due to the diagonal direction of action of the magnetic coupling (186, 190), a changed flow pattern arises at the rear of the impeller (183), and this flow pattern is crucial in terms of the radial stabilization of the pump impeller (183) in case of failure of the electromagnetic radial bearing (192, 193) and the resulting operation of the blood pump under emergency conditions.

The gap space (204) between the rear of the pump impeller (183) and the pump housing (191) located opposite from it form a flow space through which fluid flows in a retrograde manner relative to the direction of the main flow (207), from the high-pressure zone at the impeller outlet (195) through the gap space (204) as well as through rinsing channels (206) created in the impeller body (183) towards the front of the impeller (183) as a result of the above-mentioned pressure distribution at the impeller (183). This rinsing flow (210, 205), on the one hand, ensures that flow stagnations in the individual flow zones (204, 206) are avoided, thus reducing the risk of thrombi in the blood pump. On the other hand, especially the flow through the gap space (204) provides a fluid-mechanical rotor bearing that becomes effective in case of failure of the electromagnetic bearing (192, 193), said fluid-mechanical rotor bearing stabilizing the impeller (183) in the radial direction during radial deflections of the pump impeller (183) in the pump housing (180) in the manner already explained in conjunction with the fluid-mechanical rotor bearing of FIG. 1 or 2.

Therefore, with the exemplary embodiment of the blood pump according to FIGS. 7 and 8, an additional emergency-operation bearing (204, 210) is provided which altogether contributes to enhancing the operating reliability of the blood pump. Moreover, the fluid circulating in the gap space (204) displays a flow pattern that is particularly gentle on the blood since here, the rinsing flow (210, 205) is only subjected to flow deflections to a very small extent, thus largely eliminating the risk of stalling of the flow and the resultant risk of thrombi in recirculating flow zones.

The further mode of operation of the blood pump corresponds largely to that of the exemplary embodiment of the blood pump of FIGS. 1, 3, 4 and 5.

FIGS. 9, 10, 11 and 12 show a blood pump in which the pump impeller (234) in the pump housing (230) is supported in the radial direction by a hydrostatic bearing (247) and in the axial direction by means of a hydrodynamic bearing (239). The impeller (12) here is driven by an electric motor (233) and a permanent magnetic axial coupling (235, 236, 237, 238) whose structure and mode of operation correspond to that of the exemplary embodiment of the blood pump of FIGS. 1 and 2. Therefore, the above-mentioned advantages of such a drive concept also apply for the exemplary embodiment of the blood pump according to FIGS. 9 and 10.

Regarding the flow pattern inside the blood pump, the descriptions and explanations provided in the section titled "Structure and mode of operation of the blood pump" apply here. Furthermore, in the case of the blood pump according to the exemplary embodiment of FIGS. 9 and 10, the secondary flows (252, 253) acquire a central role in terms of the mode of operation of the hydrostatic rotor bearing and the hydrodynamic rotor bearing, which will be explained in greater detail below.

Due to the axial attractive forces between the driving magnets (237) and the driven magnets (238) of the permanent magnetic axial coupling (235, 236, 237, 238), an axial force is exerted on the pump impeller (234), as a result of which the impeller (234) moves towards the drive unit until its rear (239) comes into contact with the stationary pump element (240). Consequently, in order to provide a bearing for the impeller (234) in the pump housing (230), there is a need for an axial bearing that counteracts the axial attractive forces of the magnetic coupling (235, 236, 237, 238) and that limits the axial movements of the impeller (234). In the exemplary embodiment of the blood pump according to FIGS. 9 and 10, this is achieved by a hydrodynamic axial bearing at the rear of the impeller (239), whose structure and mode of operation will be described in greater detail below with reference to FIG. 10.

The fluid circulating at the rear (259) of the impeller in the exemplary embodiment of the blood pump according to FIGS. 9, 10, 11 and 12 is a rinsing flow (251, 252) that is branched off from the main flow (250) at the front (254) of the impeller and then further conveyed to the rear (259) of the impeller via a central rinsing channel (248) in the impeller body (234). When the impeller (234) rotates during operation of the blood pump, the secondary set of blades (261, 260) provided at the rear of the impeller (234) causes the rinsing flow (252) to be conveyed radially to the outside via the rinsing channels (260) as a result of the exerted centrifugal effects, from where it rejoins the main flow (250).

Figure 12:
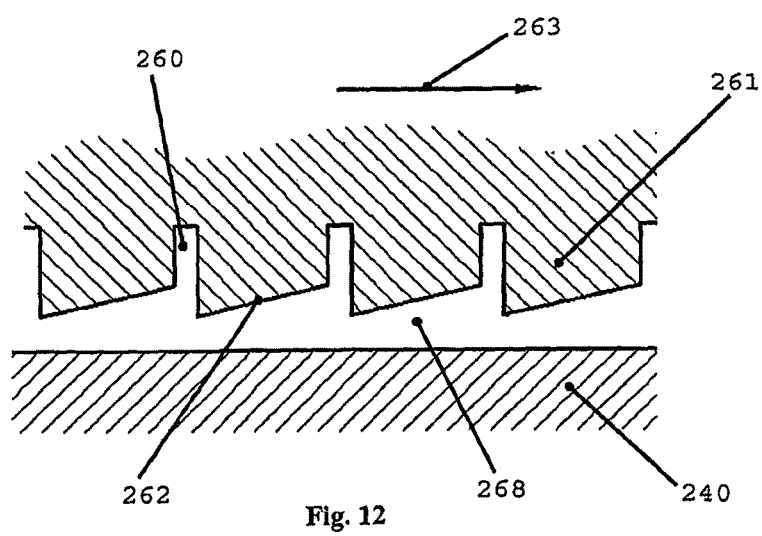
FIG. 12 is a developed cross-section view through the hydrodynamic axial bearing of FIG. 9.

The pump impeller (234) in the pump housing (230) is axially supported in such a way that the rinsing flow (252) is concurrently employed as the bearing flow for a hydrodynamic axial bearing (262, 240) at the rear of the impeller (259). In a preferred exemplary embodiment of the blood pump, the mode of operation of this hydrodynamic axial bearing is based on a taper land bearing (262), as illustrated in FIG. 12. Alternative hydrodynamic axial bearings based, for instance, on a spiral groove bearing are likewise conceivable.

In the case of a multi-surface taper land bearing, as shown in FIG. 12, the rotation of the impeller (234) causes a squeezing flow in the tapered interstices (268) which, according to the Reynolds effect, builds up a hydrodynamic carrying force in the axial direction that is directed opposite to the loading force from the magnetic coupling (237, 238) and that causes an axial lifting of the impeller (234) from the stationary pump element (240). This ensures a contact-free, hydrodynamic axial bearing of the impeller (234) in the pump housing (230).

Finally, for the radial stabilization of the impeller (234) in the pump housing (230), the hydrostatic restoring force according to the Lomakin effect is utilized which becomes active in the case of radial deflections of the impeller (234) in the pump housing (234) in the leakage flow (253) through the gap space (258) between the shroud (245) and the pump housing (230) located opposite from it, as has already been elaborated upon extensively for the exemplary embodiment of the blood pump according to FIGS. 1 and 2.

Moreover, the radial stability of the impeller (234) in the pump housing (230) is additionally increased owing to the radial restoring forces that act in the axial magnetic coupling (237, 238) in the case of radial deflections of the impeller (234). In an exemplary embodiment of the present invention, this permanent magnetic radial restoring force constitutes an effective way to center the impeller (234) in the pump housing and it assists the bearing function of the hydrostatic radial bearing (253, 258).

The major advantages of such a rotor bearing in comparison to conventional hydrodynamic rotor bearings in blood pumps are, on the one hand, the simplification of the bearing mechanism along with a reduction in the number of parts needed for the rotor bearing, so that the rotor bearing according to the exemplary embodiment of FIGS. 9 to 12 is considerably easier to implement. On the other hand, there is also the advantage that, aside from the hydrodynamic axial bearing, there is no need for any additional design measures for the rotor bearing of the pump impeller (234). Instead, the radial bearing is based on components—such as the shroud (245) and the magnetic coupling (237, 238)—and on flow patterns, that is to say, the leakage flow (253), all of which would be necessary anyway as components for a hematologically compliant blood pump. In comparison to mechanical rotor bearings subject to solid friction and wear of their bearing surfaces, the advantage of such a rotor bearing lies in its contact-free stabilization of the impeller without friction and wear, so that the service life of the blood pump can be correspondingly increased. The use of a hydrostatic radial bearing which, in contrast to hydrodynamic bearings, can be operated with a considerably wider bearing gap, ultimately also yields the advantage of such a rotor bearing, namely, that its operation is considerably gentler on the blood in comparison to a blood pump that is hydrodynamically supported on both sides (radial and axial) so that, in the final analysis, the stress on the blood and thus on the patient is considerably minimized.

Figure 13:
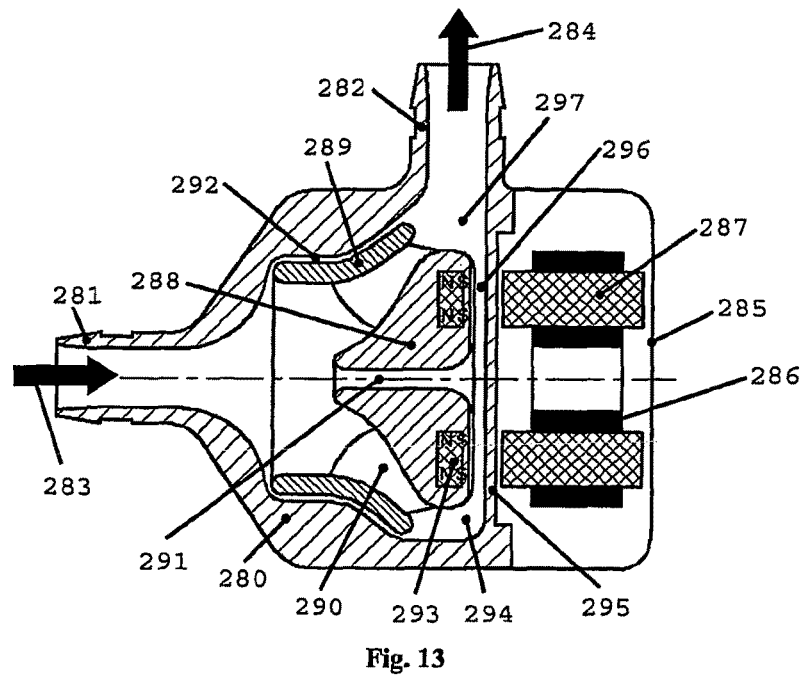
FIG. 13 is cut-away view of a blood pump with a fluid-mechanical rotor bearing in which an external electric motor with an electromagnetic axial coupling is employed as the drive according to an exemplary embodiment of the present invention.

FIG. 13 shows a blood pump having the same structure and the same mode of operation as the blood pump in FIG. 9. In FIG. 13, however, the exemplary embodiment of the blood pump is such that, in contrast to the exemplary embodiment of FIG. 9, an electromagnetic drive (285, 286, 287) is employed that is located outside of the pump housing (280) and fastened to the rear of the pump housing (295). The advantages of such an exemplary embodiment were already described in detail in conjunction with the exemplary embodiment of the blood pump according to FIG. 4 and can be directly applied to the exemplary embodiment of the blood pump according to FIG. 13.

The mode of operation of the electromagnetic axial coupling (286, 287, 293) as well as the advantages associated with this likewise correspond to those of the exemplary embodiment according to FIG. 4 and consequently also apply to the exemplary embodiment according to FIG. 13.

The mode of operation of the hydrostatic-hydrodynamic rotor bearing (292, 296) as well as the advantages associated with this can be correspondingly taken over from the exemplary embodiment according to FIG. 9.

The further mode of operation of the blood pump, particularly of the magnetic coupling device (287, 293) as well as the secondary flow patterns in the blood pump, can be largely taken over from the exemplary embodiment according to FIG. 9.

Figure 14:
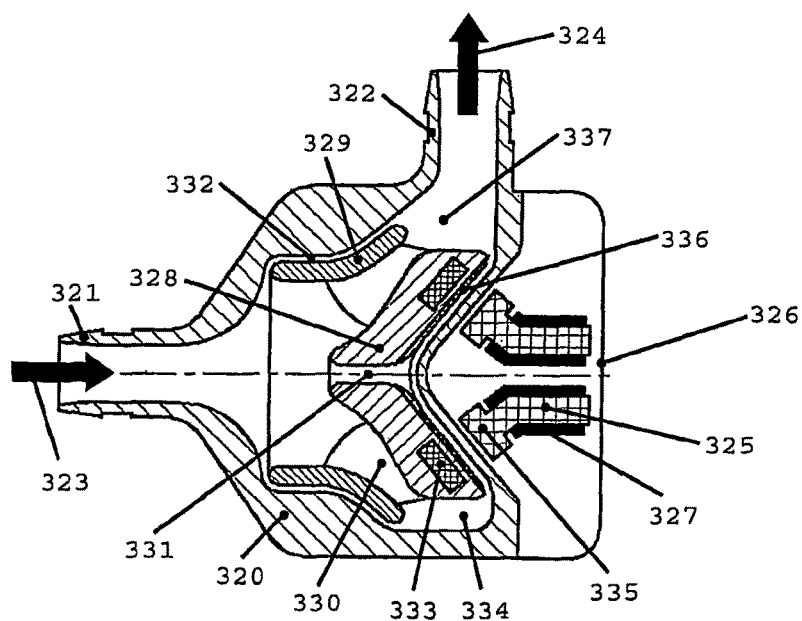
FIG. 14 is a cut-away view of a blood pump with a fluid-mechanical rotor bearing in which an external electric motor with an electromagnetic diagonal coupling is employed as the drive according to an exemplary embodiment of the present invention.

FIG. 14 shows a blood pump in which the pump impeller (328) is driven by an electromagnetic coupling (325, 327, 335, 333) that acts diagonally. The pump impeller (328) in the pump housing (320) is hydrodynamically supported here likewise in a diagonal direction and, in contrast to the exemplary embodiment of the blood pump according to FIGS. 9 and 13, combines the radial bearing and the axial bearing of the impeller (328) in one unit, whereby the hydrostatic radial bearing (332) as well as the radial restoring forces in the magnetic coupling (333, 335) account for an additional stabilization of the impeller (328) in the radial direction, thus ensuring additional reliability for the rotor bearing of the pump impeller (329) in the pump housing (320), for instance, if the hydrodynamic bearing components have not been manufactured very precisely.

Regarding the flow pattern of such a blood pump having a diagonal magnetic coupling, the same advantages as those of the exemplary embodiment of the blood pump according to FIG. 7 apply.

Concerning the mode of operation of the hydrodynamic bearing (336), the same aspects as those of the exemplary embodiment according to FIGS. 5 and 13 largely apply.

Figure 15:
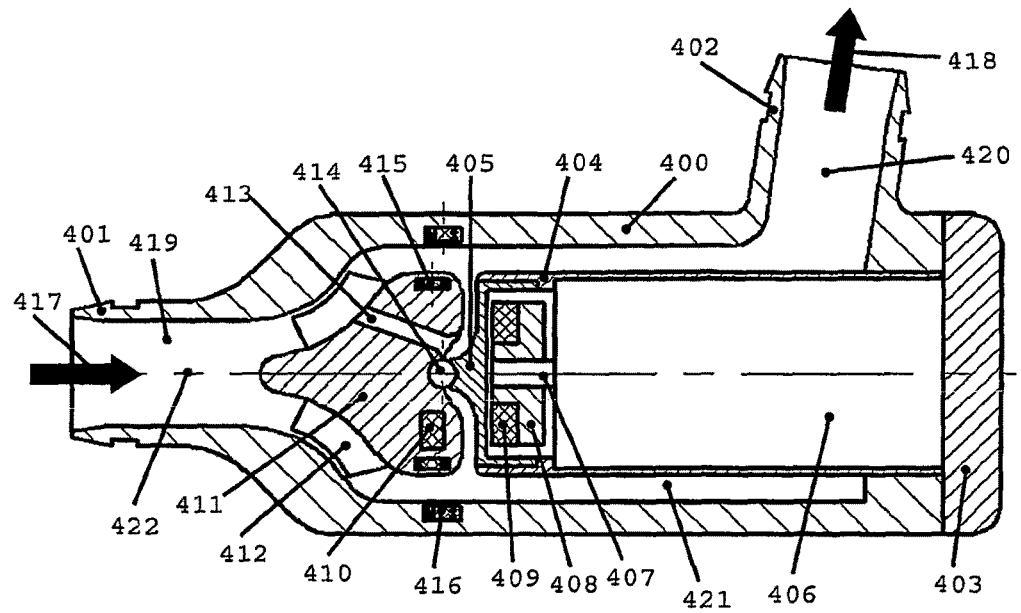
FIG. 15 is a cut-away view of a blood pump with a mechanical-magnetic rotor bearing in which the mechanical bearing and the magnetic bearing are located at the same axial height according to an exemplary embodiment of the present invention.
Figure 16:
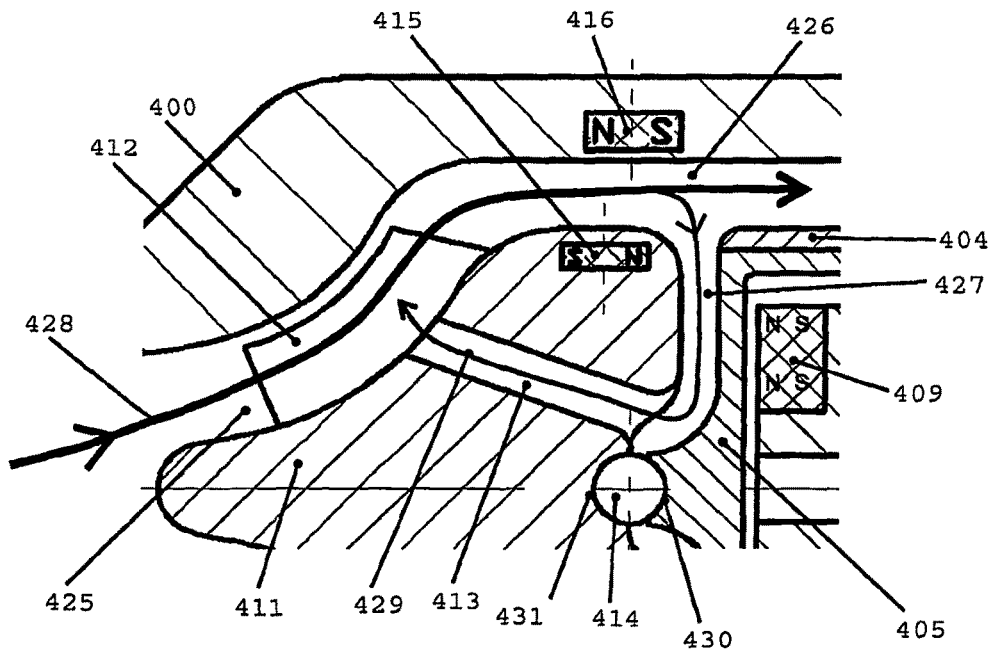
FIG. 16 is a cut-away view showing details of a flow pattern of the blood pump shown in FIG. 15 according to an exemplary embodiment of the present invention.

FIGS. 15 and 16 show a blood pump in which the rotor bearing of the pump impeller (411) in the pump housing (400) is based on a combination of mechanical bearing and permanent magnetic bearing. The impeller (12) is driven by an electric motor (406) and by a permanent magnetic axial coupling (407, 408, 409, 410) whose structure and mode of operation corresponds to the exemplary embodiment of the blood pump of FIGS. 1 and 2. Therefore, the above-mentioned advantages of such a drive concept likewise apply for the exemplary embodiment of the blood pump according to FIGS. 15 and 16.

As far as the flow pattern inside the blood pump is concerned, the descriptions and explanations provided in the section titled "Structure and mode of operation of the blood pump" apply. Moreover, the blood pump according to FIGS. 15 and 16 does not make use of a shroud, so that the leakage flow between the impeller blades (412) and the pump housing located opposite from them remains negligible, at least for the embodiment of the blood pump according to FIGS. 15 and 16.

The exemplary embodiment of the blood pump according to FIGS. 15 and 16 as well as the blood pump according to FIGS. 17 and 18, which will be described next, is still functional even if a shroud is employed. The shroud only plays a subordinated role in terms of the functionality of the blood pump and especially of its rotor bearing, which is why it is not considered at this juncture. Moreover, in the case of the blood pump according to FIG. 20, an exemplary embodiment of the blood pump with a shroud is described, which will be examined in greater detail in the following sections.

The mechanical rotor bearing in the blood pump according to FIGS. 15 and 16 comprises a thrust ball bearing or pivot bearing (405, 414), which consist of a ball (or a rotational member with a rounded tip) (414) and a spherical cap (405) as bearing elements. One of the bearing elements here constitutes the rotating bearing component that is permanently joined to the impeller body (411) while the other element, the stationary bearing component, which is permanently joined to the stationary pump element (405), is or constitutes a uniform component.

In a preferred exemplary embodiment of the blood pump, the ball (414) is the rotating bearing component while the spherical cap (405) is the stationary bearing component. Bioceramics such as aluminum oxide ($Al_2O_3$) or zirconium oxide ($ZrO_2$) as well as biocompatible plastics such as ultrahigh-molecular polyethylene (UHMW-PE), polyether ether ketone (PEEK), polyoxymethylene (POM) or polyimide (PI) as well as biocompatible metals are employed as the materials for the individual bearing components. In a preferred exemplary embodiment of the blood pump, bioceramics or biocompatible metals are used for the rotating bearing component, while bioceramics or biocompatible plastics are used for the stationary bearing component.

In the blood pump according to FIGS. 15 and 16, the axial attractive forces in the magnetic coupling (409, 410) are absorbed by the pivot bearing. Here, the pivot bearing as the thrust ball bearing is concurrently a centering radial bearing. Owing to the punctiform effect of the pivot bearing (405, 414), the impeller (411) is nevertheless subject to tilting movements around the pivot bearing which result, in particular, from the unstable attractive forces of the axial magnetic coupling (409, 410). Therefore, in order to stabilize the impeller (411) vis-à-vis tilting deflections, there is a need for a support bearing that limits the tilting movements of the impeller (411) in the pump housing (400).

In the exemplary embodiment of the blood pump according to FIGS. 15 and 16, this support bearing is created by a permanent magnetic bearing (415, 416) with which a permanent magnetic element is integrated as a stator magnet (416) into the pump housing (400) and another permanent magnetic element is integrated as a rotor magnet (415) into the impeller body. In a preferred exemplary embodiment of the blood pump, the permanent magnetic elements consist of concentrically arranged permanent magnetic rings, which are each magnetized opposite from each other in the axial direction. Rare earth magnets such as NdFeB or SmCo are preferably used as the materials for these annular magnets (415, 416).

In a preferred exemplary embodiment of the blood pump, the individual annular magnets (415, 416) are arranged concentrically with respect to each other. In the case of lateral tilting deflections of the rotor magnet (415) in the stator magnet (416), the axial restoring forces that are active between the annular magnets (415, 416) cause a stable restoring moment that puts the rotor magnets (415) back into the non-deflected position. This defines a stable support bearing against lateral tilting movements of the pump impeller (411) in the pump housing (400). Therefore, the rotor bearing of the pump impeller (411) is based on a bearing having a mixed form ("hybrid bearing"), stemming from a combination of a mechanical pivot bearing (405, 414) with a permanent magnetic support bearing (415, 416).

The axial position of the individual concentric annular magnets (415, 416) with respect to each other as well as their axial position relative to the pivot bearing (405, 414) in the blood pump according to FIGS. 15 and 16 as well as in the other bearing variants, which will still be elaborated upon, are instrumental for the stability of the rotor bearing.

In the exemplary embodiment of the blood pump according to FIGS. 15 and 16, the pivot bearing (405, 414) (center point of the ball) is at the same axial height as the rotor magnet (415). The stator magnet (416) here is likewise at the same axial height as the rotor magnet (415). This constellation is already sufficient to ensure a virtually stable bearing of the pump impeller (411) in the pump housing (400).

In this context, it should be taken into account that the pivot bearing (405, 414) only constitutes a unilaterally active axial thrust bearing and the bearing ball (414) consequently has to stay in the spherical cap (405) since the radial centering of the pump impeller (411) in the pump housing (400) is no longer present if the bearing ball (414) slips out of the spherical cap (405) due to unstable radial attractive forces between the rotor magnet (415) and the stator magnet (416). For these reasons, for instance, an axially shifted placement of the stator magnet (416) in the direction of the pump inlet does not translate into a useful rotor bearing under the conditions at hand.

Moreover, the slipping of the pivot bearing (405, 414) is also promoted by the hydraulic flow forces (axial shear) that act on the impeller (411) during operation of the pump, said forces causing the impeller (411) to lift from the pivot bearing (405, 414). In the current state of the art of blood pumps having a pivot bearing as the only axial bearing, this risk of the pivot bearing slipping out and lifting poses a heightened safety hazard for the operation of the pump since, if the pivot bearing slips out, this not only causes undesired noise due to the uncontrolled movement of the rotor in the pump housing but, under certain circumstances, can even considerably impair the build-up of flow and pressure as the main function of the blood pump.

The risk of slippage in the current state of the art is countered by the axial attractive forces of the magnetic coupling. Nevertheless, extreme operating points involving a great pressure build-up in the blood pump can cause the magnitude of the hydraulic flow forces to exceed the attractive forces of the magnetic coupling, so that a stable bearing of the impeller in the pump housing is no longer present.

In the inventive exemplary embodiment of the blood pump according to FIGS. 15 and 16, in contrast, the axial restoring forces in the magnetic bearing (415, 416) not only provide a support bearing against tilting deflections but also an axial bearing that acts alternatingly, so that the risk of the pivot bearing slipping out is effectively prevented.

Another advantageous special aspect of the blood pump according to FIGS. 15 and 16 is that, while the concentric arrangement of the magnetic bearing (415, 416) and of the pivot bearing is retained, a greater rotor stability of the impeller (411) can be achieved if the stator magnet (416) is positioned axially offset by a certain distance in the direction of the magnetic coupling (409, 410), as can be seen in FIG. 16. The axial distance of the offset of the stator magnet (416) relative to the rotor magnet (415) amounts to between 1% and 50%, in a preferred embodiment between 5% and 25%, of the axial dimension of the stator magnet (416).

The axial forces active in the magnetic bearing (415, 416) are absorbed as a preload by the pivot bearing (405, 406). Due to such a positioning of the stator magnet (416), on the one hand, the preloaded axial forces between the rotor magnet (415) and the stator magnet (416) cause the tilting stiffness of the magnetic bearing (415, 416) to be further increased, as a result of which the lateral tilting movements can be further restricted and the rotor stability can thus be raised. On the other hand, such a constellation also correspondingly brings about a permanent magnetic axial bearing with greater bearing stiffness for the pump impeller (411), which further limits the risk of the pump impeller (411) slipping out of the pivot bearing (405, 406), thus maintaining rotor stability even in those extreme applications that are characterized by a high pressure build-up in the blood pump. In extracorporeal applications of the blood pump within the scope of a heart-lung machine (HLM) or within the scope of an ECMO system where the pressure has to build up to levels of up to 800 mmHg, such a bearing concept can be effectively employed and, thanks to the simple construction of the blood pump, with very little manufacturing effort.

The fluid circulation at the rear of the impeller (427) and of the pivot bearing (405, 414) is effectuated by the rinsing flow (429) already described in FIG. 1 and by the rinsing channels (413) provided for this purpose in the impeller body (411) so that, on the one hand, flow stagnations at the rear of the impeller (427) are prevented and, on the other hand, the friction heat of the pivot bearing (405, 414) is effectively dissipated so that ultimately, the blood pump can be altogether operated in a manner that is gentle on the blood.

Figure 17:
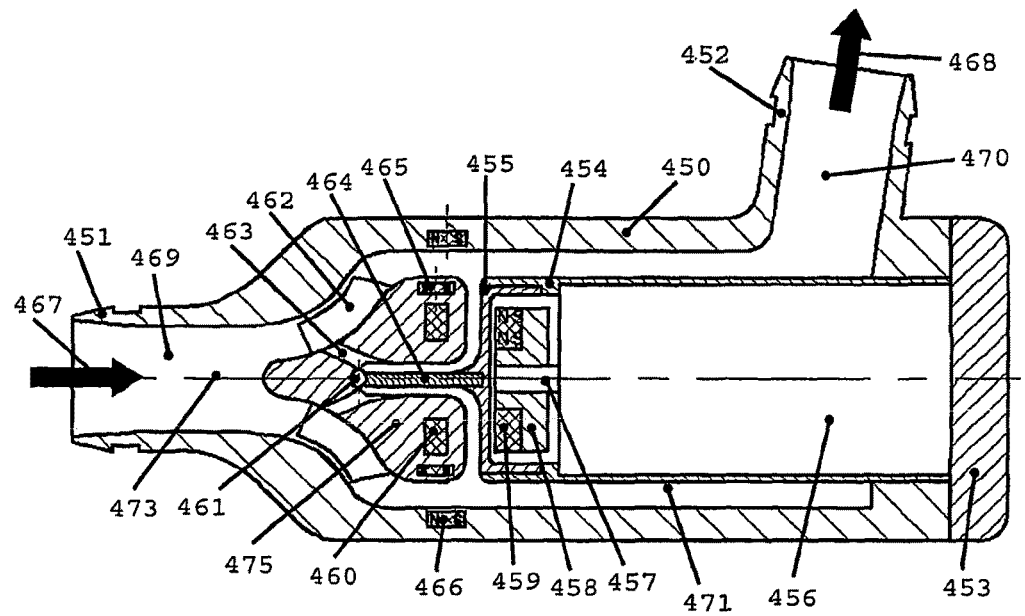
FIG. 17 is a cut-away view of a blood pump with a mechanical-magnetic rotor bearing in which the mechanical bearing and the magnetic bearing are located at different axial heights according to an exemplary embodiment of the present invention.
Figure 18:
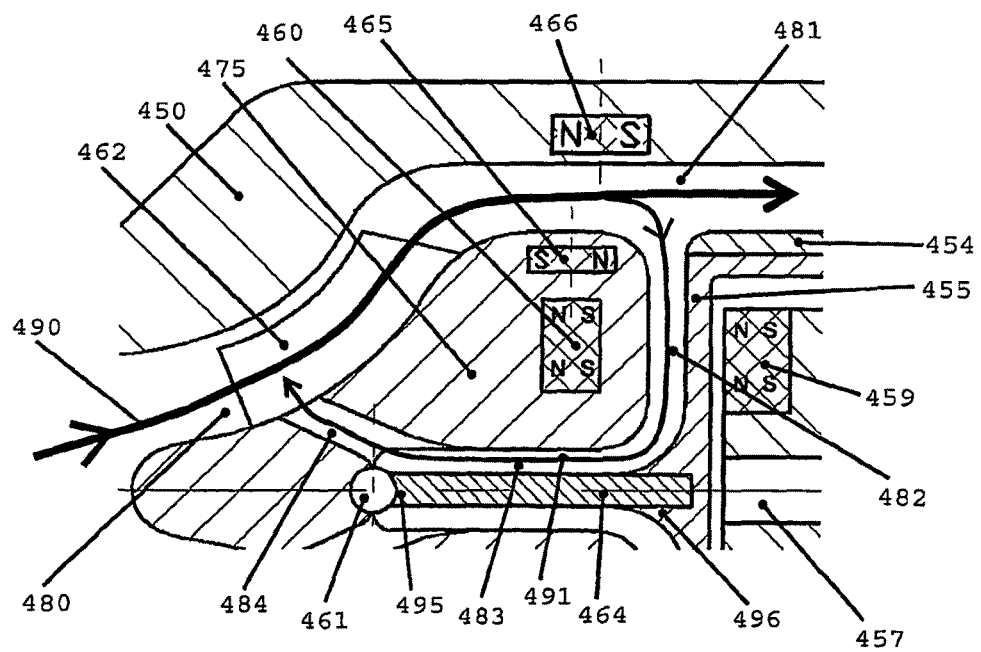
FIG. 18 is a cut-away view showing details of a flow pattern of the blood pump shown in FIG. 17 according to an exemplary embodiment of the present invention.
Figure 19:
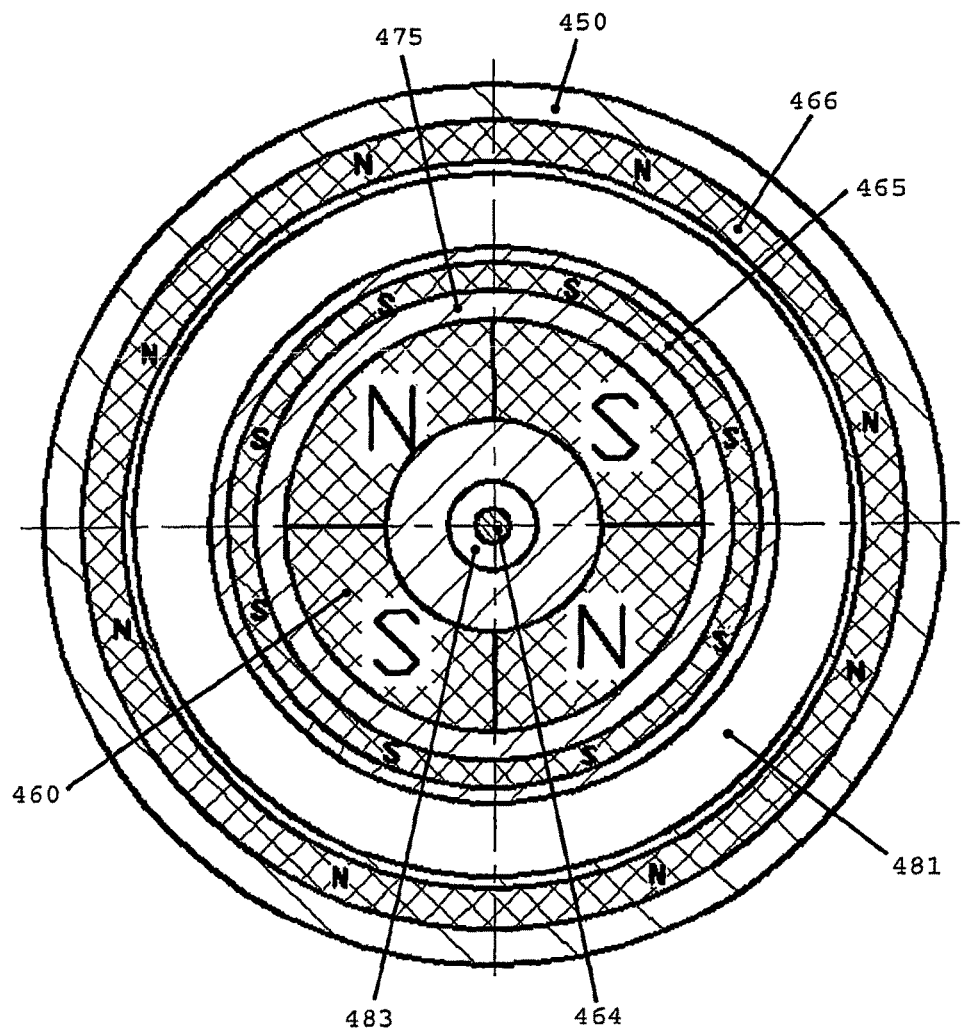
FIG. 19 is a cross-section view through the impeller and the magnetic bearing of FIG. 18.

FIGS. 17, 18 and 19 show a blood pump in which the rotor bearing of the pump impeller (475) in the pump housing (450) is based on a combination of a mechanical bearing and a permanent magnetic bearing, whereby, in contrast to the exemplary embodiment of the blood pump according to FIGS. 15 and 16, the mechanical bearing (461, 495) is located at a different axial height with respect to the permanent magnetic bearing (465, 466).

The structure and mode of operation of this exemplary embodiment largely correspond to that of the blood pump of FIGS. 15 and 16. This applies particularly to the drive unit (456, 457, 458, 459), to the coupling device (457, 458, 459, 460), to the flow pattern inside the pump as well as to the structure and mode of operation of the magnetic bearing (465, 466).

In this context, FIG. 19 shows the magnetization of the individual coupling and bearing magnets in a sectional view through the blood pump.

Therefore, the above-mentioned advantages pertaining to the above-mentioned pump components likewise apply to the exemplary embodiment of the blood pump according to FIG. 17.

In the exemplary embodiment of the blood pump according to FIGS. 17, 18 and 19, however, a different exemplary embodiment of the rotor bearing is shown in which the axial position of the mechanical pivot bearing (461, 495) relative to the permanent magnetic thrust bearing (465, 466) is axially offset in the direction of the pump inlet (451). The pivot bearing (461, 495) here is likewise based on a bearing ball (461) joined to the impeller body (475) and on a spherical cap (495) that is joined to the stationary pump element (455) via an elongated axis (464).

The mode of operation of the pivot bearing (461, 495) essentially corresponds to the mode of operation of the pivot bearing of FIGS. 15 and 16. The same applies to the selection of the materials for the individual bearing components.

The impeller (475) of the blood pump according to FIGS. 17, 18 and 19 is stabilized against lateral tilting movements around the pivot bearing (461, 495), likewise by a permanent magnetic support bearing (465, 466) in which the rotor magnet (465) is integrated into the impeller body (475) and the stator magnet (466) is embedded in the pump housing (450). Regarding the selection of the magnetic materials, the same statements made for the blood pump of FIGS. 15 and 16 apply.

The essential difference between the blood pump of FIG. 17 and the blood pump of FIG. 15 is that, owing to the different axial position of the magnetic bearing (465, 466) and of the pivot bearing (461, 495), during the stabilization of the impeller (475) against tilting movements, the magnetic bearing (465, 466) works with a considerably larger lever arm (corresponding to the axial distance between the magnetic bearing and the pivot bearing), and consequently, the magnetic restoring moments needed to stabilize the impeller (475) can be considerably increased while the magnetic force conditions between the rotor magnet (465) and the stator magnet (466) are the same, and the stability of the rotor bearing increases accordingly.

In the case of the blood pump according to FIG. 17, it is ensured that the blood is conveyed gently since fluid circulates at the rear of the impeller (482) and especially in the pivot bearing (461, 495) by means of the rinsing flow (491).

In order to further secure the pump impeller (475) against slipping out of the pivot bearing (461, 495), the blood pump according to FIG. 17 offers the possibility to position the stator magnet (466) axially offset with respect to the rotor magnet (465), so that the stabilization of the impeller (475) can be adapted to the specific clinical requirements, while the bearing load in the pivot bearing (461, 495) can be concurrently minimized by adapting the individual axial distances.

Figure 20:
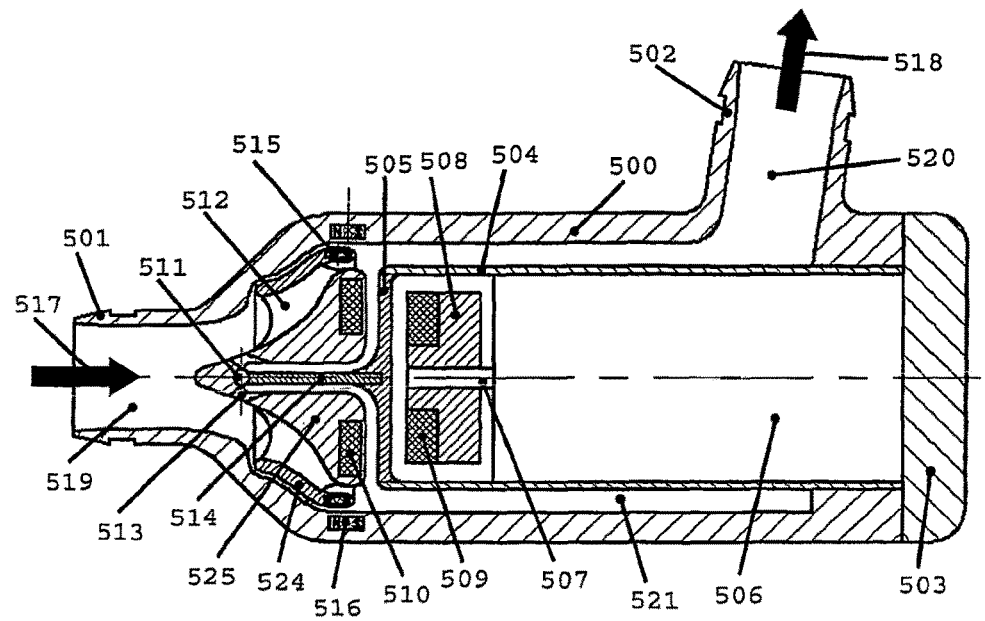
FIG. 20 is a cut-away view of a blood pump with a mechanical-magnetic rotor bearing in which the magnetic bearing is integrated into the shroud according to an exemplary embodiment of the present invention.
Figure 21:
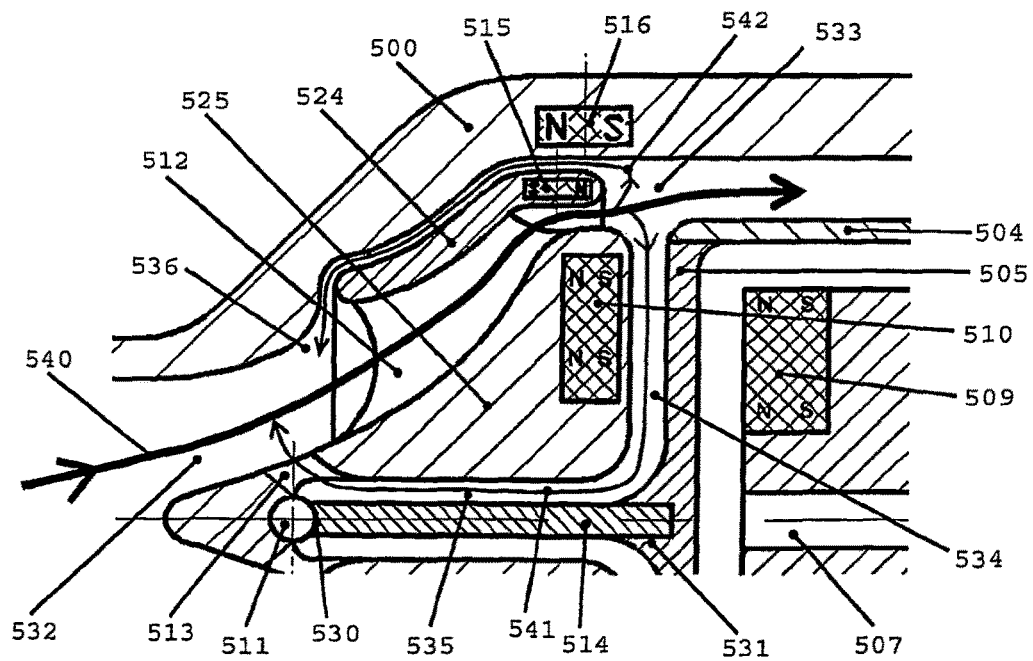
FIG. 21 is a cut-away view showing details of a flow pattern of the blood pump shown in FIG. 20, according to an exemplary embodiment of the present invention.

FIGS. 20 and 21 show a blood pump whose structure and mode of operation largely correspond to that of the exemplary embodiment of the blood pump of FIG. 17. The positioning of the magnetic bearing (515, 516) in the blood pump according to FIG. 20, however, is not in the impeller body (525) itself but rather in the shroud (524). This affords another possibility to raise the carrying force of the magnetic support bearing (515, 516), thus further enhancing the stability of the impeller (525) since the air gap between the rotor magnet (515) and the stator magnet (516) is diminished in comparison to that of the blood pump of FIG. 17, thus raising the bearing forces that act in the magnetic bearing (515, 516) accordingly.

For the rest, the structure and mode of operation are largely the same as those of the blood pump of FIG. 17, so that the advantages associated with this can be taken over here.

FIGS. 22 to 31 show a blood pump whose structure is very similar to that of the blood pump of FIG. 20. However, the essential difference of the blood pump according to FIG. 20 is that, for purposes of stabilizing the impeller (625) against tilting movements around the pivot bearing, a magnetically acting bearing is employed that was already implemented in the diagonal coupling used. Accordingly, a synergism exists here between the coupling device and the bearing device which essentially eliminates the need for a separate magnetic bearing to stabilize the impeller against tilting, and the magnetic diagonal coupling is employed for driving purposes as well as for bearing purposes.

With such an exemplary embodiment, on the one hand, the blood pump has a simple structure and mode of operation, which increases the operating safety of the blood pump accordingly. On the other hand, the blood pump is altogether considerably more compact, thus also entailing advantages in terms of the implantation of such a blood pump.

Figure 23:
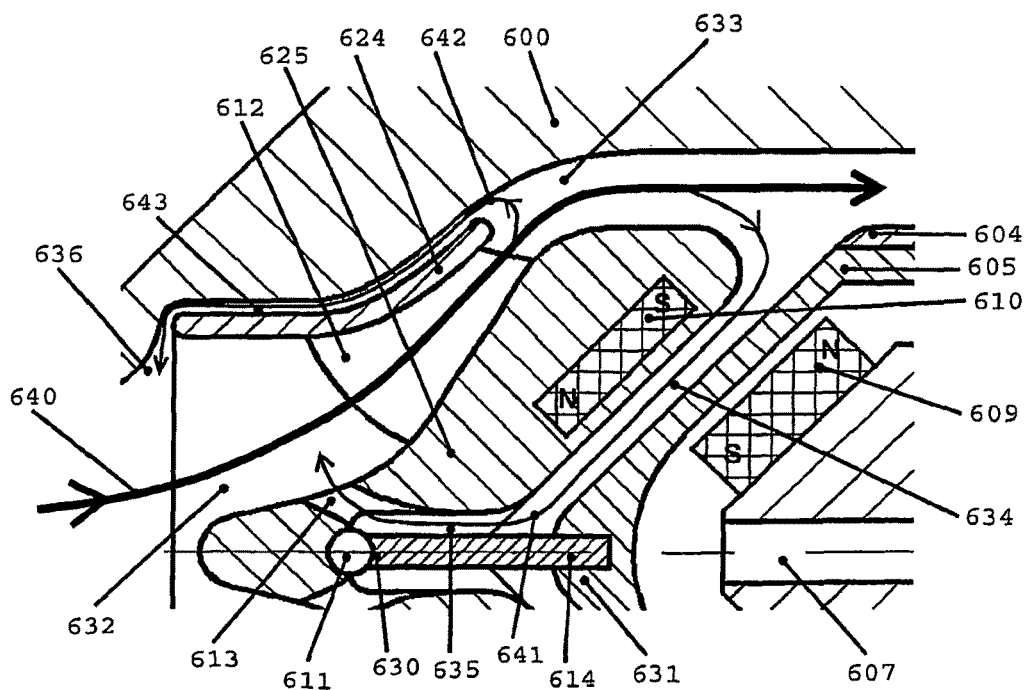
FIG. 23 is a cut-away view showing details of a flow pattern of the blood pump shown in FIG. 22, according to an exemplary embodiment of the present invention.
Figure 24:
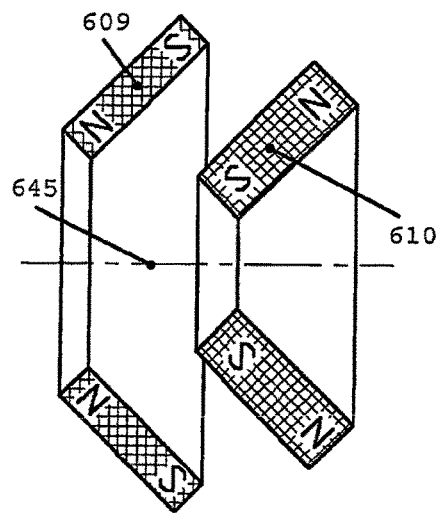
FIG. 24 is a diagram showing a diagonal coupling of FIG. 22, without a separation of the coupling magnets.
Figure 25:
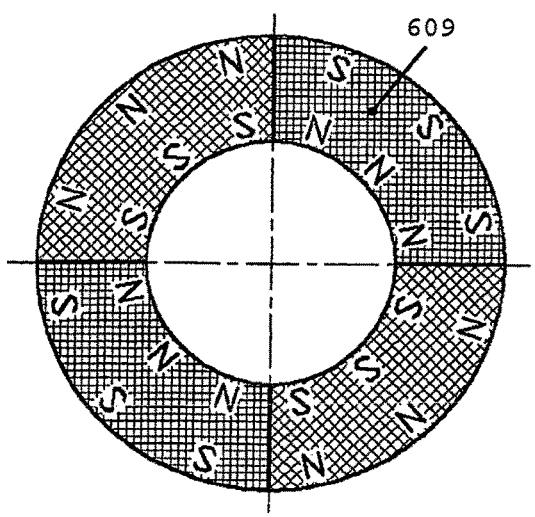
FIG. 25 is a cross-section view through the diagonal coupling of FIG. 24.
Figure 26:
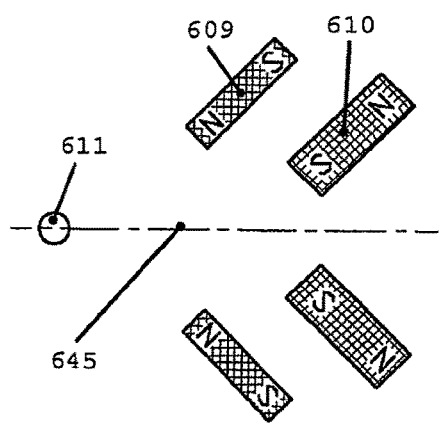
FIG. 26 is a diagram showing the diagonal coupling of FIG. 24 in a state of balance.
Figure 27:
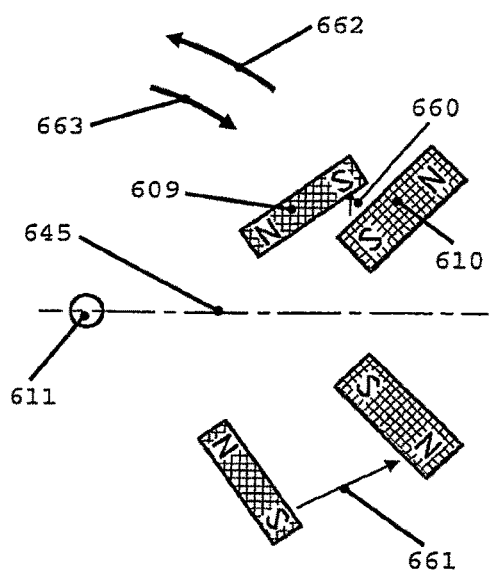
FIG. 27 is a diagram showing the diagonal coupling of FIG. 24 in a deflected position, and the bearing forces that are thus active in the diagonal coupling.
Figure 32:
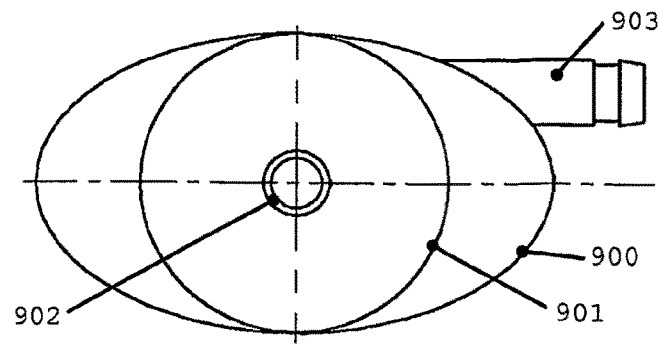
FIG. 32 is a diagram of a blood pump with an elliptical pump design.
Figure 33:
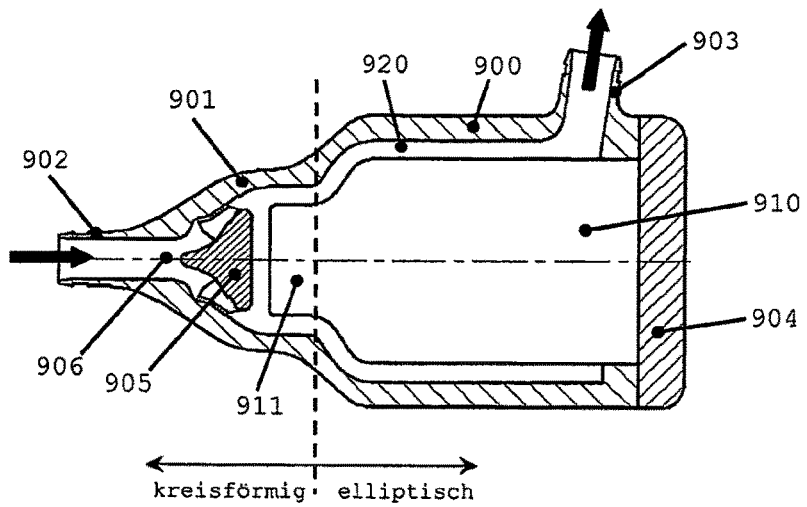
FIG. 33 is a cross-section view of the blood pump with an elliptical pump design shown in FIG. 32.

The advantageous properties of a diagonal coupling with respect to the flow pattern as well as other aspects can be taken over from the discussion of the blood pump according to FIGS. 7 and 14. FIG. 23 shows a detailed view of the flow pattern in the blood pump according to FIG. 22.

FIGS. 24 to 27 show the structure and mode of operation of the rotor bearing integrated into the diagonal coupling in the case of tilting movements of the impeller around the pivot bearing. Here, the individual magnet segments are configured very simply in the radial direction.

The separation of the magnet segments in the radial direction as well as the mode of operation resulting from this are illustrated in FIGS. 28 to 31. The separation of the coupling magnets in the radial direction as well as the joining of two individual magnet segments at their radial ends in the opposite polarization direction cause the magnetic field lines to be compacted along the separation line, as a result of which higher moments can be transmitted and the stabilization effect of the diagonal coupling is reinforced, which is particularly clear in FIG. 31.

Consequently, the operating safety of the blood pump can be effectively increased by such a separation of the coupling magnets, whereby the manufacturing effort needed for such a system can be correspondingly lowered in view of the simple and uncomplicated components.

These advantages particularly fulfill the requirements made by medical technology in terms of a very high level of reliability and maximum reduction of the effort involved with the medical products to be employed.

FIGS. 32 to 35 show a blood pump which, irrespective of the concept chosen for the rotor bearing, has an outer shape that amounts to a "harmonious flat design". The term "harmonious flat design" refers to a pump geometry whose cross sectional dimension perpendicular to the rotational axis (906) has a height-to-width ratio H/W<1. The essential advantage of such an exemplary embodiment is that it is easier to implant the blood pump into the appropriate regions of the human body. Especially in the case of a subcutaneous placement of the blood pump, which is preferred in medical technology with an eye towards attaining "minimally invasive systems", it is then possible to achieve tremendous clinical advantages, which can be essentially summarized as follows:

they are patient-friendly since it involves minimal surgical procedures;

they are easy to remove in cases of temporary implantation over medium-term periods of use such as, for instance, with the bridge-to-recovery concept;

they are easy to access for diagnostic checking of the pump, particularly in the case of critical pump operation, as well as easier replacement of the pump with a new one.

By way of example of a harmonious flat design of the pump housing (900), FIGS. 32 to 35 show a blood pump having an elliptical cross section, whereby the area of the pump housing (901) associated with the impeller (905)—at least in the interior of the pump housing (901)—can be configured so as to be circular-cylindrical, whereas the area (910) associated with the drive can be elliptical. In case a permanent magnetic coupling device is used, the space (911) intended for the coupling device can also be configured to be circular-cylindrical, at least in the interior of the pump housing.

Especially the exemplary embodiment of the housing area (910) associated with the drive as an elliptical cross section not only retains the above-mentioned advantages of a blood pump that can be implanted subcutaneously, but also a drive, particularly on the basis of an electric motor, that accounts for a higher capacity of the elliptical blood pump in comparison to a circular-cylindrical pump having a similar diameter.

Figure 34:
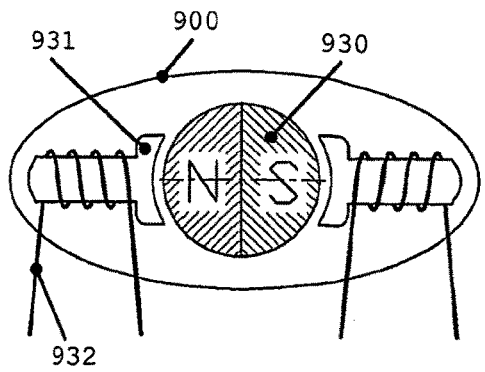
FIG. 34 is a cross-section view through the elliptical motor in the 2-phase version.
Figure 35:
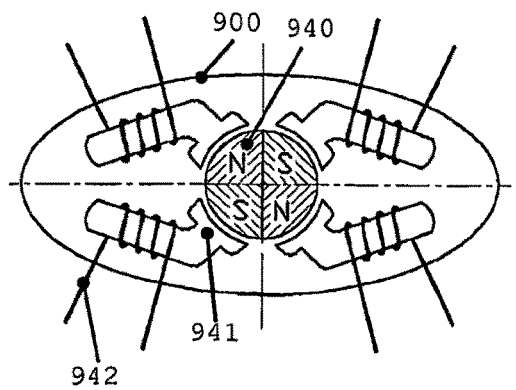
FIG. 35 is a cross-section view through the elliptical motor in the 4-phase version.

The essential advantage of a drive unit having a harmonious flat design is that, when an electric motor having, for example, an elliptical cross section is used, as is shown in FIGS. 34 and 35, the capacity of the pump is greater than with other pumps of a comparable diameter. For instance, when an elliptical pump and motor design—whereby the ellipsis has the main dimensions width W and height H wherein H<W—is compared to a conventional circular-cylindrical pump design having the diameter D, that is to say, H=D (smallest dimensions that are relevant in terms of accessibility, insertability during the implantation procedure and better suitability for subcutaneous applications), the elliptical design of the motor entails the following advantages over the circular-cylindrical design because of the more efficient utilization of the elliptical spaces for the motor windings (932, 934) and for the stator units (931, 941):

generation of a higher maximum moment and thus also an expansion of the achievable operating range of the pump;

lower electricity consumption and thus less power demand for the blood pump (battery operation being particularly relevant in this context);

higher overall efficiency and thus more efficient operation of the blood pump.

These advantages can also be expressed differently as:

a blood pump with a smaller elliptical diameter (H<D) yields the same hemodynamic capacity as a circular-cylindrical pump with a large diameter.

Particularly with axial blood pumps and diagonal blood pumps that have primarily an axially elongated shape, such an exemplary embodiment of the blood pump has advantages in terms of the capacity of the blood pumps as well as advantages that are clinically relevant for operating the blood pump in a manner that is gentle on the patient.

FIG. 36 shows an exemplary embodiment in which the blood pump can be detached from the drive unit (1050, 1070, 1071, 1072) as a separate pump head (1000) so that the drive unit (1050, 1070, 1071, 1072)—which is a component of the blood pump system that is relatively complex to produce—can be re-used, whereas the pump head (1000)—as a disposable part that is easy to produce—can be replaced after every clinical use. Particularly in the case of extracorporeal applications (HLM, ECMO, etc.), this exemplary embodiment entails commensurate advantages over short-term to medium-term periods of use.

In this context, all of the exemplary embodiments of the blood pump that are particularly easy to manufacture are suitable as the pump head (1000). This applies especially to exemplary embodiments of the blood pump with a mechanical rotor bearing according to FIGS. 15 to 31. The possibilities of the increased pressure build-up, concurrently ensuring sufficient rotor stability with the exemplary embodiment of the blood pump according to FIGS. 15, 17 and 20, predestine these exemplary embodiments of the blood pump particularly for such extracorporeal applications (HLM, ECMO, etc.) in which there is a need for a high pressure build-up in the blood pump.

Here, the moments can be transferred from the drive unit (1050, 1070, 1071, 1072) to the pump impeller via a permanent magnetic or an electromagnetic coupling device. The drive unit (1050, 1070, 1071, 1072) is accommodated in its entirety in a drive housing (1060) and closed off by a housing cover at an end that can be opened and closed so that the drive unit (1050, 1070, 1071, 1072) can be installed and removed. This cover of the drive unit (1050, 1070, 1071, 1072) ensures that the drive unit (1050, 1070, 1071, 1072) remains protected against impurities from the environment. Cooling fins (1061) can be created on the outer surface of the pump housing (1060) for purposes of effectively dissipating the motor heat. In this exemplary embodiment, the blood pump can be deployed particularly efficiently for short-term to medium-term applications in the realm of extracorporeal blood circulation.

FIGS. 37, 38 and 39 show an exemplary embodiment in which the blood pump is driven as a separable (disposable) pump head (1100) by a separate pneumatically operated turbine (1170).

The pump head (1100) can be joined to the drive unit (1060), for example, by a turn lock (1120, 1164) with which the pump head (1100) can be separated from the drive unit (1160) quickly and easily.

Within the scope of the exemplary embodiment according to FIG. 37, the moments are transmitted from the turbine (1170) to the pump impeller (1100), preferably by a permanent magnetic coupling device (1178, 1179) that is rigidly joined to the turbine (1170) via the drive shaft (1172).

The mode of operation of the turbine (1170) is essentially the same as that of a gas turbine known from the general state of the art, whose dimensions are adapted to the pump head (1100).

This drive concept entails several advantages, especially for all of those applications of the extracorporeal circulation in which the turbine is driven by a supply of high-pressure oxygen. The special feature of oxygen as the source of driving energy consists, on the one hand, of the fact that oxygen is available in every operating room and is almost every hospital ward. In this context, FIG. 38 schematically depicts the use of such a pump and drive system on a patient. The impeller rotational speed can be adapted to the requisite operating conditions using a manually or automatically regulated valve (2030). The goal of such an adaptation would be only the extracorporeal perfusion of certain organs with blood that stems from the patient herself/himself or that is additionally administered to the patient in the form of a transfusion.

Another practical use of this pump and drive concept is illustrated in FIG. 39. Here, the combination of the blood pump with a blood oxygenation system (oxygenator) makes use of an appropriate synergism in which oxygen is employed to oxygenate the blood as well as to drive the pump. Particularly in the case of short-term to medium-term applications (heart-lung machines, ECMO, etc.), such a drive concept can be used considerably more effectively than conventional perfusion systems.

Another special feature of such a drive concept lies in the separate configuration of the blood pump, which constitutes a blood-conveyance system that can be employed independently of the oxygenator. Separating the oxygen-driven blood pump from the oxygenator (unit) has the advantage that the blood pump presented here can be used with any desired oxygenator and therefore, the cardiology technician is not forced to use a specific oxygenator prescribed by the manufacturer of the blood pump. Such a modular perfusion concept especially entails advantages with respect to the efficiency of the perfusion system.

FIG. 40 shows the use of a blood pump as an implantable VAD system.

FIG. 41 shows the use of a blood pump for extracorporeal circulation in combination with an oxygenator during ECMO use in a small child.

LIST OF REFERENCE NUMERALS 1 pump housing
2 pump inlet
3 pump outlet
4 housing cover
5 electric motor
6 motor shaft
7 motor housing
8 pole shoe of the magnetic coupling
9 driving magnets
10 motor cover, stationary pump element
11 driven magnets
12 pump impeller
13 impeller blades
14 feed channel
15 guide channel between the electric motor and the pump housing
16 rotor magnet of the permanent magnetic bearing
17 stator magnet of the permanent magnetic bearing
18 shroud
19 stator unit of the electromagnetic radial bearing
20 rotor unit of the electromagnetic radial bearing
21 blood flow into the pump
22 blood flow out of the pump
23 rotational axis
30 rinsing channel in the impeller body
31 axial gap space at the rear of the impeller
32 radial gap space of the leakage flow
33 rear of the impeller
34 main flow
35 leakage flow
36 branch-off point of the rinsing flow from the main flow
37 entrance of the leakage flow channel
38 exit of the leakage flow channel
39 rinsing flow in the rinsing channel
40 high-pressure zone at the impeller outlet
41 flow channel at the front of the impeller
42 rinsing flow in the axial gap space at the rear of the impeller
43 impeller body, impeller hub
70 pump housing
71 impeller inlet
72 impeller outlet
73 pump impeller
74 driven magnets
75 stator magnet of the drive
76 windings of the drive
77 motor housing
78 motor cover, stationary pump element
79 pump cover
80 rotor magnet of the permanent magnetic bearing
81 stator magnet of the permanent magnetic bearing
82 rotor unit of the electromagnetic radial bearing
83 stator unit of the electromagnetic radial bearing
84 guide channel
100 pump housing
101 pump inlet
102 pump outlet
103 pump impeller
104 blood flow into the pump
105 blood flow out of the pump
106 driven magnets
107 stator magnet of the drive
108 windings of the drive
109 motor housing
110 stator magnet of the permanent magnetic bearing
111 rotor magnet of the permanent magnetic bearing
112 rotor unit of the electromagnetic radial bearing
113 stator unit of the electromagnetic radial bearing
114 rear part of the pump housing
115 high-pressure zone at the impeller outlet
116 lateral flow space between the impeller and the housing
130 pump housing
131 pump inlet
132 pump outlet
133 pump impeller
134 blood flow into the pump
135 blood flow out of the pump
136 driven magnets
137 stator magnet of the drive
138 windings of the drive
139 motor housing
140 stator magnet of the drive
141 pump housing
142 rotor unit of the electromagnetic radial bearing
143 stator unit of the electromagnetic radial bearing
144 pump housing
145 high-pressure zone at the impeller outlet
146 pump housing
147 lateral flow space between the impeller and the housing
148 flow channel in the pump outlet
149 impeller blades
150 shroud
151 pump impeller
152 rinsing channel
153 rinsing channel
154 rinsing channel
155 rinsing flow
156 rinsing channel in the impeller body
157 main flow
158 main flow
159 leakage flow
160 rinsing flow
180 pump housing
181 pump inlet
182 pump outlet
183 pump impeller
184 blood flow into the pump
185 blood flow out of the pump
186 driven magnets
187 stator magnet of the drive
188 windings of the drive
189 motor housing
190 stator magnet of the drive
191 pump housing
192 rotor unit of the electromagnetic radial bearing
193 stator unit of the electromagnetic radial bearing
194 pump housing
195 high-pressure zone at the impeller outlet
196 pump housing
197 lateral flow space between the impeller and the housing
198 flow channel in the pump outlet
199 impeller blades
200 shroud
204 rinsing channel
205 rinsing flow
206 rinsing channel
207 leakage flow
208 main flow
209 leakage flow
210 rinsing flow
230 pump housing
231 pump inlet 232 pump outlet
233 electric motor
234 pump impeller
235 motor shaft
236 pole shoe
237 driving magnets
238 driven magnets
239 hydrodynamic axial bearing
240 motor cover, stationary pump element
241 motor housing
242 pump cover
243 impeller blades
245 shroud
246 flow space at the front of the impeller
247 fluid-mechanical radial stabilization
248 rinsing channel in the impeller body
249 flow channel in the pump inlet
250 main flow
251 rinsing flow
252 rinsing flow
253 leakage flow
254 front of the impeller
255 high-pressure zone at the impeller outlet
256 entrance of the leakage channel
257 exit of the leakage channel
258 radial gap space between the impeller and the pump housing
259 flow space at the rear of the impeller
260 secondary set of blades
261 flow space for the secondary set of blades
262 tapered surfaces of the hydrodynamic axial bearing
263 rotational direction of the impeller
265 blood flow into the pump
266 blood flow out of the pump
267 guide channel
268 tapered interstice of the hydrodynamic bearing
280 pump housing
281 pump inlet
282 pump outlet
283 blood flow into the pump
284 blood flow out of the pump
285 motor housing
286 windings of the drive
287 stator magnet of the drive
288 pump impeller
289 shroud
290 impeller blades
291 rinsing channel in the impeller body
292 fluid-mechanical radial stabilization
293 driven magnets
294 lateral flow space between the impeller and the housing
295 pump housing
296 hydrodynamic axial bearing
297 high-pressure zone at the impeller outlet
320 pump housing
321 pump inlet
322 pump outlet
323 blood flow into the pump
324 blood flow out of the pump
325 stator magnet of the drive
326 motor housing
327 windings of the drive
328 pump impeller
329 shroud
330 impeller blades
331 rinsing channel in the impeller body
332 fluid-mechanical radial stabilization
333 driven magnets
334 lateral flow space between the impeller and the housing
335 stator magnet of the drive
336 hydrodynamic axial bearing
337 high-pressure zone at the impeller outlet
400 pump housing
401 pump inlet
402 pump outlet
403 pump cover
404 motor housing
405 spherical cap
406 electric motor
407 motor shaft
408 pole shoe
409 driving magnets
410 driven magnets
411 pump impeller
412 impeller blades
413 rinsing channel in the impeller body
414 bearing ball
415 rotor magnet of the permanent magnetic bearing
416 stator magnet of the permanent magnetic bearing
417 blood flow into the pump
418 blood flow out of the pump
419 flow channel in the pump inlet
419 flow channel in the pump outlet
421 guide channel
422 rotational axis
425 front of impeller
426 high-pressure zone at the impeller outlet
427 flow space at the rear of the impeller
428 main flow
429 rinsing flow
430 spherical cap, rear of pivot
431 front of pivot
450 pump housing
451 pump inlet
452 pump outlet
453 pump cover
454 motor housing
455 motor cover, stationary pump element
456 electric motor
457 motor shaft
458 pole shoe
459 driving magnets
460 driven magnets
461 bearing balls
462 impeller blades
463 rinsing channel in the impeller body
464 bearing axis
465 rotor magnet of the permanent magnetic bearing
466 stator magnet of the permanent magnetic bearing
467 blood flow into the pump
468 blood flow out of the pump
469 flow channel in the pump inlet
470 flow channel in the pump outlet
471 guide channel
473 rotational axis
475 pump impeller
480 front of impeller
481 high-pressure zone at the impeller outlet
482 flow space at the rear of the impeller
483 central rinsing channel
490 main flow
491 rinsing flow
495 spherical cap
496 tip of the motor cover 500 pump housing
501 pump inlet
502 pump outlet
503 pump cover
504 motor housing
505 motor cover, stationary pump element
506 electric motor
507 motor shaft
508 pole shoe
509 driving magnets
510 driven magnets
511 bearing balls
512 impeller blades
513 rinsing channel in the impeller body
514 bearing axis
515 rotor magnet of the permanent magnetic bearing
516 stator magnet of the permanent magnetic bearing
517 blood flow into the pump
518 blood flow out of the pump
519 flow channel in the pump inlet
520 flow channel in the pump outlet
521 guide channel
524 shroud
525 pump impeller
530 spherical cap
531 tip of the motor cover
532 front of impeller
533 high-pressure zone at the impeller outlet
534 flow space at the rear of the impeller
535 central rinsing channel
536 exit of the leakage flow
540 main flow
541 rinsing flow
542 leakage flow
600 pump housing
601 pump inlet
602 pump outlet
603 pump cover
604 motor housing
605 motor cover, stationary pump element
606 electric motor
607 motor shaft
608 pole shoe
609 driving magnets
610 driven magnets
611 bearing balls
612 impeller blades
613 rinsing channel in the impeller body
614 bearing axis
617 blood flow into the pump
618 blood flow out of the pump
619 flow channel in the pump inlet
620 flow channel in the pump outlet
621 guide channel
624 shroud
625 pump impeller
630 spherical cap
631 tip of the motor cover
632 front of impeller
633 high-pressure zone at the impeller outlet
634 flow space at the rear of the impeller
635 central rinsing channel
636 exit of the leakage flow
640 main flow
641 rinsing flow
642 leakage flow
645 rotational axis
660 restoring force between the driving magnets and the driven magnets in the constricted air gap
661 restoring force between the driving magnets and the driven magnets in the enlarged air gap
662 restoring force on the driven magnets during tilting of the impeller
663 deflection moment on the driven magnets during tilting of the impeller
670 first driven magnet with separation of the coupling magnet segments in the radial direction
671 second driven magnet with separation of the coupling magnet segments in the radial direction
672 first driving magnet with separation of the coupling magnet segments in the radial direction
673 second driving magnet with separation of the coupling magnet segments in the radial direction
680 restoring force between the driving magnets and the driven magnets in the constricted air gap with separation of the coupling magnet segments
681 restoring force between the driving magnets and the driven magnets in the enlarged air gap with separation of the coupling magnet segments
682 restoring moment on the separate driven magnets during tilting of the impeller
683 deflection moment on the separate driven magnets during tilting of the impeller
900 elliptical part of the pump housing
901 circular-cylindrical part of the pump housing
902 pump inlet
903 pump outlet
904 pump cover
905 pump impeller
906 feed channel
910 elliptical part of the drive unit
911 circular-cylindrical part of the drive unit
930 rotor magnet in a 2-pole electromagnetic drive
931 stator magnet in a 2-pole electromagnetic drive with an elliptical cross section
932 windings in a 2-pole electromagnetic drive with an elliptical cross section
940 rotor magnet in a 4-pole electromagnetic drive with an elliptical cross section
941 stator magnet in a 4-pole electromagnetic drive with an elliptical cross section
942 windings in a 4-pole electromagnetic drive with an elliptical cross section
1000 blood pump as a separable pump unit
1020 turn lock on the pump unit
1060 drive housing
1061 cooling fins
1062 turn lock on the drive unit
1063 motor cover
1064 drive cover
1070 drive magnets
1071 pole shoe
1072 motor shaft
1100 blood pump as a separable pump unit
1120 turn lock on the pump unit
1160 drive housing
1161 oxygen inlet
1162 oxygen outlet
1163 drive cover
1164 turn lock on the drive unit
1170 gas turbine
1171 turbine blades
1172 drive shaft
1173 rotational axis 1174 first roller bearing
1175 second roller bearing
1176 first support plate
1177 second support plate
1178 pole shoe
1179 drive magnets
1180 interior of the drive unit through which oxygen flows
1181 flow channel on the inlet side
1182 flow channel on the outlet side
1190 incoming oxygen
1191 oxygen flow inside the drive unit
1192 outgoing oxygen
2000 blood pump
2010 turbine
2020 magnetic coupling
2030 flow control valve
2040 oxygen tank
2050 compressor
2060 patient
2100 blood pump
2110 turbine
2120 magnetic coupling
2130 flow control valve
2140 oxygen tank
2150 compressor
2160 patient
2170 oxygenator
2180 flow control valve

What is claimed is:

1. A blood pump, comprising:
a blade impeller with a rotational axis in a pump housing;
the blade impeller comprising an impeller body, impeller blades, and a shroud, said shroud being permanently joined to the impeller blades at the outer rim of the blade contour;
a main flow being provided between the impeller body and the shroud;
  a first element that comprises a fluid-mechanical radial bearing based on a Lomakin effect between the shroud and the pump housing;
  a second element physically separated from the first element, the second element comprising a radial magnetic bearing, the radial magnetic bearing comprising an electromagnetic radial bearing or a permanent magnetic radial bearing and the radial magnetic bearing is formed by a magnetic coupling;
the blood pump comprising an hydrodynamic axial bearing between the impeller and the pump housing, the hydrodynamic axial bearing being based on fluid-mechanical forces;
the impeller body exhibits a central rinsing channel;
the blade impeller comprising a secondary set of blades, the secondary set of blades being provided at a rear of the impeller;
the secondary set of blades inducing another centrifugal flow in such a manner that, due to the centrifugal forces that act in the secondary set of blades, a portion of the main flow is branched off as rinsing flow via a rinsing channel and is conveyed in a side space radially towards the outside until the rinsing flow finally once again enters the main flow in a high-pressure zone at the impeller outlet; and
the impeller being axially supported in the pump housing in such a way that the rinsing flow is concurrently employed as a bearing flow for the hydrodynamic axial bearing.

2. The blood pump recited in claim 1, wherein the radial magnetic bearing comprises at least two annular magnets.

3. The blood pump recited in claim 2, wherein at least one of the annular magnets is integrated into the impeller and/or into one of the components of the impeller.

4. The blood pump recited in claim 1, wherein the radial magnetic bearing is configured as a separate permanent magnetic radial bearing.

5. The blood pump recited in claim 1, wherein the radial magnetic bearing is configured as a separate electromagnetic radial bearing.

6. The blood pump recited in claim 5, wherein the radial magnetic bearing has a rotor magnet in the impeller and a stator magnet in the pump housing.

7. The blood pump recited in claim 1, wherein the magnetic coupling is an axial magnetic coupling.

8. The blood pump recited in claim 1, wherein the magnetic coupling is a diagonal magnetic coupling.

9. The blood pump recited in claim 1, wherein the radial magnetic bearing exerts regulated electromagnetic forces.

10. The blood pump recited in claim 1, wherein the Lomakin effect is operational between the impeller and the pump housing.

11. The blood pump recited in claim 1, wherein the Lomakin effect is operational between the shroud and the pump housing.

12. The blood pump recited in claim 1, wherein the impeller has an additional axial bearing.

13. The blood pump recited in claim 12, wherein the additional axial bearing of the impeller is based on permanent magnetic forces.

14. The blood pump recited in claim 12, wherein the additional axial bearing of the impeller is based on electromagnetic forces.

15. The blood pump recited in claim 12, wherein the additional axial bearing of the impeller is based on fluid-mechanical forces.

16. The blood pump recited in claim 12, wherein the additional axial bearing at a rear of the impeller is based on hydraulic forces.

17. The blood pump recited in claim 1, wherein the blood pump comprises a separable pump head and a re-usable drive unit.

18. The blood pump recited in claim 17, wherein the separable pump head is disposable.

19. The blood pump recited in claim 1, wherein an additional set of blades is provided at the rear of the impeller.

* * * * *